US008926606B2

(12) United States Patent
Davalos et al.

(10) Patent No.: US 8,926,606 B2
(45) Date of Patent: Jan. 6, 2015

(54) INTEGRATION OF VERY SHORT ELECTRIC PULSES FOR MINIMALLY TO NONINVASIVE ELECTROPORATION

(75) Inventors: Rafael Davalos, Blacksburg, VA (US); Christopher B. Arena, Denver, NC (US); John Caldwell, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 732 days.

(21) Appl. No.: 12/757,901

(22) Filed: Apr. 9, 2010

(65) Prior Publication Data

US 2010/0261994 A1     Oct. 14, 2010

Related U.S. Application Data

(60) Provisional application No. 61/167,997, filed on Apr. 9, 2009, provisional application No. 61/285,618, filed on Dec. 11, 2009.

(51) Int. Cl.
| A61B 18/04 | (2006.01) |
| A61N 1/32 | (2006.01) |
| A61B 18/14 | (2006.01) |
| A61N 1/04 | (2006.01) |
| A61B 18/00 | (2006.01) |

(52) U.S. Cl.
CPC .......... *A61N 1/327* (2013.01); *A61B 18/1477* (2013.01); *A61N 1/0412* (2013.01); *A61B 2018/00613* (2013.01); *A61B 2018/0016* (2013.01); *A61N 1/0424* (2013.01)
USPC ........................................................ 606/41

(58) Field of Classification Search
CPC ...... A61N 1/0412; A61N 1/327; A61B 18/14; A61B 18/1206; A61B 2018/0016; A61B 2018/00613
USPC ................................................ 606/27, 34, 41
See application file for complete search history.

(56) References Cited

U.S. PATENT DOCUMENTS

| 1,653,819 A | 12/1927 | Northcott et al. |
| 4,016,886 A | 4/1977 | Doss |

(Continued)

FOREIGN PATENT DOCUMENTS

| DE | 863111 | 1/1953 |
| DE | 863111tr | 1/1953 |

(Continued)

OTHER PUBLICATIONS

Al-Sakere, B. et al., 2007, "Tumor ablation with irreversible electroporation." PLoS ONE 2.

(Continued)

*Primary Examiner* — Michael Peffley
*Assistant Examiner* — Daniel Fowler
(74) *Attorney, Agent, or Firm* — New River Valley IP Law, PC; Michele L. Mayberry

(57) ABSTRACT

The present invention provides methods, devices, and systems for in vivo treatment of cell proliferative disorders. The invention can be used to treat solid tumors, such as brain tumors. The methods rely on non-thermal irreversible electroporation (IRE) or supra-poration to cause cell death in treated tumors. In embodiments, the methods comprise the integration of ultra-short electric pulses, both temporally and spatially, to achieve the desired modality of cell death.

27 Claims, 17 Drawing Sheets

FIG. 5

(56) References Cited

U.S. PATENT DOCUMENTS

| | | |
|---|---|---|
| 4,226,246 A | 10/1980 | Fragnet |
| 4,262,672 A | 4/1981 | Kief |
| 4,407,943 A | 10/1983 | Cole et al. |
| 4,416,276 A * | 11/1983 | Newton et al. .................. 606/35 |
| 4,810,963 A | 3/1989 | Blake-Coleman et al. |
| 4,822,470 A | 4/1989 | Chang |
| 4,907,601 A | 3/1990 | Frick |
| 4,946,793 A | 8/1990 | Marshall, III |
| 5,019,034 A | 5/1991 | Weaver et al. |
| 5,052,391 A | 10/1991 | Silberstone et al. |
| 5,058,605 A | 10/1991 | Slovak |
| 5,098,843 A | 3/1992 | Calvin |
| 5,134,070 A | 7/1992 | Casnig |
| 5,173,158 A | 12/1992 | Schmuckler |
| 5,192,312 A | 3/1993 | Orton |
| 5,193,537 A | 3/1993 | Freeman |
| 5,273,525 A | 12/1993 | Hofmann |
| 5,283,194 A | 2/1994 | Schmuckler |
| 5,318,563 A | 6/1994 | Malis et al. |
| 5,328,451 A | 7/1994 | Davis et al. |
| 5,389,069 A | 2/1995 | Weaver |
| 5,403,311 A | 4/1995 | Abele et al. |
| 5,425,752 A | 6/1995 | Vu'Nguyen |
| 5,439,440 A | 8/1995 | Hofmann |
| 5,458,625 A | 10/1995 | Kendall |
| 5,533,999 A | 7/1996 | Hood et al. |
| 5,536,240 A | 7/1996 | Edwards et al. |
| 5,575,811 A | 11/1996 | Reid et al. |
| 5,626,146 A | 5/1997 | Barber et al. |
| 5,634,899 A | 6/1997 | Shapland et al. |
| 5,674,267 A | 10/1997 | Mir et al. |
| 5,702,359 A | 12/1997 | Hofmann |
| 5,718,246 A | 2/1998 | Vona |
| 5,720,921 A | 2/1998 | Meserol |
| 5,778,894 A | 7/1998 | Dorogi et al. |
| 5,782,882 A | 7/1998 | Lerman et al. |
| 5,800,378 A | 9/1998 | Edwards et al. |
| 5,810,762 A | 9/1998 | Hofmann |
| 5,836,905 A | 11/1998 | Lemelson et al. |
| 5,843,026 A | 12/1998 | Edwards et al. |
| 5,843,182 A | 12/1998 | Goldstein |
| 5,873,849 A | 2/1999 | Bernard |
| 5,919,142 A | 7/1999 | Boone et al. |
| 5,947,889 A | 9/1999 | Hehrlein |
| 5,983,131 A | 11/1999 | Weaver et al. |
| 5,991,697 A | 11/1999 | Nelson et al. |
| 5,999,847 A | 12/1999 | Elstrom |
| 6,009,347 A | 12/1999 | Hofmann |
| 6,010,613 A | 1/2000 | Walters et al. |
| 6,016,452 A | 1/2000 | Kasevich |
| 6,029,090 A | 2/2000 | Herbst |
| 6,041,252 A | 3/2000 | Walker et al. |
| 6,055,453 A | 4/2000 | Hofmann et al. |
| 6,068,650 A | 5/2000 | Hofmann et al. |
| 6,085,115 A | 7/2000 | Weaver et al. |
| 6,090,106 A | 7/2000 | Goble et al. |
| 6,102,885 A | 8/2000 | Bass |
| 6,106,521 A | 8/2000 | Blewett et al. |
| 6,109,270 A | 8/2000 | Mah et al. |
| 6,122,599 A | 9/2000 | Mehta |
| 6,132,419 A | 10/2000 | Hofmann |
| 6,159,163 A | 12/2000 | Strauss et al. |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann |
| 6,219,577 B1 | 4/2001 | Brown et al. |
| 6,241,702 B1 | 6/2001 | Lundquist et al. |
| 6,241,725 B1 | 6/2001 | Cosman |
| 6,261,831 B1 | 7/2001 | Agee |
| 6,278,895 B1 | 8/2001 | Bernard |
| 6,300,108 B1 | 10/2001 | Rubinsky |
| 6,326,177 B1 | 12/2001 | Schoenbach et al. |
| 6,347,247 B1 | 2/2002 | Dev et al. |
| 6,349,233 B1 | 2/2002 | Adams |
| 6,351,674 B2 | 2/2002 | Silverstone |
| 6,387,671 B1 | 5/2002 | Rubinsky |
| 6,403,348 B1 | 6/2002 | Rubinsky et al. |
| 6,470,211 B1 | 10/2002 | Ideker et al. |
| 6,482,619 B1 | 11/2002 | Rubinsky |
| 6,493,592 B1 | 12/2002 | Leonard et al. |
| 6,500,173 B2 | 12/2002 | Underwood |
| 6,526,320 B2 | 2/2003 | Mitchell |
| 6,562,604 B2 | 5/2003 | Rubinsky |
| 6,607,529 B1 | 8/2003 | Jones et al. |
| 6,611,706 B2 | 8/2003 | Avrahami et al. |
| 6,613,211 B1 | 9/2003 | McCormick et al. |
| 6,627,421 B1 | 9/2003 | Unger et al. |
| 6,653,091 B1 | 11/2003 | Dunn et al. |
| 6,669,691 B1 | 12/2003 | Taimisto |
| 6,678,558 B1 | 1/2004 | Dimmer et al. |
| 6,692,493 B2 | 2/2004 | McGovern et al. |
| 6,697,669 B2 | 2/2004 | Dev et al. |
| 6,697,670 B2 | 2/2004 | Chornenky et al. |
| 6,702,808 B1 | 3/2004 | Kreindel |
| 6,795,728 B2 | 9/2004 | Chornenky et al. |
| 6,801,804 B2 | 10/2004 | Miller et al. |
| 6,865,416 B2 | 3/2005 | Dev et al. |
| 6,892,099 B2 | 5/2005 | Jaafar et al. |
| 6,912,417 B1 | 6/2005 | Bernard et al. |
| 6,927,049 B2 | 8/2005 | Rubinsky et al. |
| 6,962,587 B2 | 11/2005 | Johnson et al. |
| 6,972,014 B2 | 12/2005 | Eum et al. |
| 6,994,706 B2 | 2/2006 | Chornenky et al. |
| 7,053,063 B2 | 5/2006 | Rubinsky et al. |
| 7,054,685 B2 | 5/2006 | Dimmer et al. |
| 7,063,698 B2 | 6/2006 | Whayne et al. |
| 7,113,821 B1 * | 9/2006 | Sun et al. ........................ 604/21 |
| 7,130,697 B2 | 10/2006 | Chornenky et al. |
| 7,211,083 B2 | 5/2007 | Chornenky et al. |
| 7,267,676 B2 | 9/2007 | Chornenky et al. |
| 7,344,533 B2 | 3/2008 | Pearson et al. |
| 7,655,004 B2 | 2/2010 | Long |
| 7,674,249 B2 | 3/2010 | Ivorra et al. |
| 7,680,543 B2 | 3/2010 | Azure |
| 7,718,409 B2 | 5/2010 | Rubinsky et al. |
| 7,951,582 B2 | 5/2011 | Gazit et al. |
| 7,955,827 B2 | 6/2011 | Rubinsky et al. |
| 8,048,067 B2 | 11/2011 | Davalos et al. |
| 8,114,070 B2 | 2/2012 | Rubinsky et al. |
| 8,162,918 B2 | 4/2012 | Ivorra et al. |
| 8,282,631 B2 | 10/2012 | Davalos et al. |
| 8,298,222 B2 | 10/2012 | Rubinsky et al. |
| 8,348,921 B2 | 1/2013 | Ivorra et al. |
| 8,465,484 B2 | 6/2013 | Davalos et al. |
| 8,603,087 B2 | 12/2013 | Rubinsky et al. |
| 8,835,166 B2 | 9/2014 | Phillips et al. |
| 2001/0044596 A1 | 11/2001 | Jaafar |
| 2001/0046706 A1 | 11/2001 | Rubinsky et al. |
| 2001/0051366 A1 | 12/2001 | Rubinsky et al. |
| 2002/0010491 A1 | 1/2002 | Schoenbach et al. |
| 2002/0055731 A1 | 5/2002 | Atala et al. |
| 2002/0077676 A1 | 6/2002 | Schroeppel et al. |
| 2002/0099323 A1 | 7/2002 | Dev et al. |
| 2002/0115208 A1 | 8/2002 | Mitchell et al. |
| 2002/0119437 A1 | 8/2002 | Grooms et al. |
| 2002/0137121 A1 | 9/2002 | Rubinsky et al. |
| 2002/0138117 A1 | 9/2002 | Son |
| 2002/0183684 A1 | 12/2002 | Dev et al. |
| 2002/0193831 A1 | 12/2002 | Smith, III |
| 2003/0009110 A1 | 1/2003 | Tu et al. |
| 2003/0060856 A1 | 3/2003 | Chornenky et al. |
| 2003/0088189 A1 | 5/2003 | Tu et al. |
| 2003/0096407 A1 | 5/2003 | Atala et al. |
| 2003/0130711 A1 | 7/2003 | Pearson et al. |
| 2003/0166181 A1 | 9/2003 | Rubinsky et al. |
| 2003/0170898 A1 | 9/2003 | Gundersen et al. |
| 2003/0194808 A1 | 10/2003 | Rubinsky et al. |
| 2003/0199050 A1 | 10/2003 | Mangano et al. |
| 2003/0208200 A1 | 11/2003 | Palanker et al. |
| 2003/0225360 A1 | 12/2003 | Eppstein et al. |
| 2004/0009459 A1 | 1/2004 | Anderson et al. |
| 2004/0019371 A1 | 1/2004 | Jaafar et al. |
| 2004/0059389 A1 | 3/2004 | Chornenky et al. |

(56) References Cited

U.S. PATENT DOCUMENTS

| | | |
|---|---|---|
| 2004/0146877 A1 | 7/2004 | Diss et al. |
| 2004/0153057 A1 | 8/2004 | Davison |
| 2004/0176855 A1 | 9/2004 | Badylak |
| 2004/0193097 A1 | 9/2004 | Hofmann et al. |
| 2004/0236376 A1 | 11/2004 | Miklavcic et al. |
| 2004/0243107 A1 | 12/2004 | Macoviak |
| 2004/0267189 A1 | 12/2004 | Mavor et al. |
| 2005/0013870 A1 | 1/2005 | Freyman et al. |
| 2005/0043726 A1 | 2/2005 | McHale et al. |
| 2005/0049541 A1 | 3/2005 | Behar et al. |
| 2005/0165393 A1 | 7/2005 | Eppstein |
| 2005/0171523 A1 | 8/2005 | Rubinsky et al. |
| 2005/0171574 A1 | 8/2005 | Rubinsky et al. |
| 2005/0182462 A1 | 8/2005 | Chornenky |
| 2005/0261672 A1 | 11/2005 | Deem et al. |
| 2005/0282284 A1 | 12/2005 | Rubinsky et al. |
| 2005/0288730 A1 | 12/2005 | Deem et al. |
| 2006/0015147 A1 | 1/2006 | Persson et al. |
| 2006/0024359 A1 | 2/2006 | Walker et al. |
| 2006/0025760 A1 | 2/2006 | Podhajsky |
| 2006/0079883 A1 | 4/2006 | Elmouelhi et al. |
| 2006/0121610 A1 | 6/2006 | Rubinsky et al. |
| 2006/0142801 A1 | 6/2006 | Demarais et al. |
| 2006/0212078 A1 | 9/2006 | Demarais et al. |
| 2006/0217703 A1 | 9/2006 | Chornenky |
| 2006/0235474 A1 | 10/2006 | Demarais |
| 2006/0264752 A1 | 11/2006 | Rubinsky et al. |
| 2006/0264807 A1 | 11/2006 | Westersten et al. |
| 2006/0269531 A1 | 11/2006 | Beebe et al. |
| 2006/0293713 A1 | 12/2006 | Rubinsky et al. |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2007/0021803 A1 | 1/2007 | Deem |
| 2007/0025919 A1* | 2/2007 | Deem et al. ............... 424/45 |
| 2007/0043345 A1 | 2/2007 | Davalos et al. |
| 2007/0060989 A1 | 3/2007 | Deem et al. |
| 2007/0118069 A1 | 5/2007 | Persson et al. |
| 2007/0156135 A1 | 7/2007 | Rubinsky et al. |
| 2007/0230757 A1 | 10/2007 | Trachtenberg et al. |
| 2007/0287950 A1 | 12/2007 | Kjeken et al. |
| 2008/0015571 A1 | 1/2008 | Rubinsky et al. |
| 2008/0021371 A1 | 1/2008 | Rubinsky et al. |
| 2008/0033340 A1 | 2/2008 | Heller et al. |
| 2008/0033417 A1 | 2/2008 | Nields et al. |
| 2008/0045880 A1 | 2/2008 | Kjeken et al. |
| 2008/0052786 A1 | 2/2008 | Lin et al. |
| 2008/0071262 A1 | 3/2008 | Azure |
| 2008/0097422 A1 | 4/2008 | Edwards et al. |
| 2008/0103529 A1 | 5/2008 | Schoenbach et al. |
| 2008/0132884 A1 | 6/2008 | Rubinsky et al. |
| 2008/0132885 A1 | 6/2008 | Rubinsky et al. |
| 2008/0200912 A1* | 8/2008 | Long ............... 606/37 |
| 2008/0214986 A1 | 9/2008 | Ivorra et al. |
| 2008/0269586 A1 | 10/2008 | Rubinsky et al. |
| 2009/0024075 A1 | 1/2009 | Schroeppel et al. |
| 2009/0029407 A1 | 1/2009 | Gazit et al. |
| 2009/0062788 A1* | 3/2009 | Long et al. ............... 606/41 |
| 2009/0198231 A1 | 8/2009 | Esser et al. |
| 2009/0247933 A1 | 10/2009 | Maor et al. |
| 2009/0248012 A1 | 10/2009 | Maor et al. |
| 2009/0269317 A1 | 10/2009 | Davalos |
| 2009/0281477 A1 | 11/2009 | Mikus et al. |
| 2009/0292342 A1 | 11/2009 | Rubinsky et al. |
| 2009/0318905 A1 | 12/2009 | Bhargav et al. |
| 2009/0326436 A1 | 12/2009 | Rubinsky et al. |
| 2010/0023004 A1 | 1/2010 | Francischelli et al. |
| 2010/0030211 A1 | 2/2010 | Davalos et al. |
| 2010/0049190 A1 | 2/2010 | Long et al. |
| 2010/0087813 A1 | 4/2010 | Long |
| 2010/0130975 A1 | 5/2010 | Long |
| 2010/0152725 A1 | 6/2010 | Pearson et al. |
| 2010/0160850 A1 | 6/2010 | Ivorra et al. |
| 2010/0179530 A1 | 7/2010 | Long et al. |
| 2010/0196984 A1 | 8/2010 | Rubinsky et al. |
| 2010/0204560 A1 | 8/2010 | Salahieh et al. |
| 2010/0204638 A1 | 8/2010 | Hobbs et al. |
| 2010/0249771 A1 | 9/2010 | Pearson et al. |
| 2010/0250209 A1 | 9/2010 | Pearson et al. |
| 2010/0255795 A1 | 10/2010 | Rubinsky et al. |
| 2010/0256630 A1 | 10/2010 | Hamilton, Jr. et al. |
| 2010/0261994 A1 | 10/2010 | Davalos et al. |
| 2010/0331758 A1 | 12/2010 | Davalos et al. |
| 2011/0034209 A1 | 2/2011 | Rubinsky et al. |
| 2011/0106221 A1 | 5/2011 | Neal, II et al. |
| 2011/0118732 A1 | 5/2011 | Rubinsky et al. |
| 2011/0217730 A1 | 9/2011 | Gazit et al. |
| 2012/0034131 A1 | 2/2012 | Rubinsky et al. |
| 2012/0071872 A1 | 3/2012 | Rubinsky et al. |
| 2012/0071874 A1 | 3/2012 | Davalos et al. |
| 2012/0089009 A1 | 4/2012 | Omary et al. |
| 2012/0109122 A1 | 5/2012 | Arena et al. |
| 2012/0179091 A1 | 7/2012 | Ivorra et al. |
| 2012/0226218 A1 | 9/2012 | Phillips et al. |
| 2012/0277741 A1 | 11/2012 | Davalos et al. |
| 2013/0090646 A1 | 4/2013 | Moss et al. |
| 2013/0108667 A1 | 5/2013 | Soikum et al. |
| 2013/0184702 A1 | 7/2013 | Neal, II et al. |
| 2013/0196441 A1 | 8/2013 | Rubinsky et al. |
| 2013/0197425 A1 | 8/2013 | Golberg et al. |
| 2013/0202766 A1 | 8/2013 | Rubinsky et al. |
| 2013/0253415 A1 | 9/2013 | Sano et al. |
| 2013/0281968 A1 | 10/2013 | Davalos et al. |
| 2013/0345779 A1 | 12/2013 | Maor et al. |
| 2014/0088578 A1 | 3/2014 | Rubinsky et al. |
| 2014/0163551 A1 | 6/2014 | Maor et al. |

FOREIGN PATENT DOCUMENTS

| | | |
|---|---|---|
| DE | 4000893 | 7/1991 |
| DE | 4000893tr | 7/1991 |
| EP | 0378132 | 7/1990 |
| EP | 0935482 A | 8/1999 |
| EP | 0935482 | 5/2005 |
| EP | 0935482 B1 | 5/2005 |
| WO | 9639531 | 12/1996 |
| WO | 9814238 | 4/1998 |
| WO | 9814238 A | 4/1998 |
| WO | 0020554 | 4/2000 |
| WO | 0107584 | 2/2001 |
| WO | 0107585 | 2/2001 |
| WO | 0110319 A | 2/2001 |
| WO | WO 01/07583 | 2/2001 |
| WO | WO 01/10319 | 2/2001 |
| WO | WO0148153 | 7/2001 |
| WO | 0181533 | 11/2001 |
| WO | WO 02/78527 | 10/2002 |
| WO | 02089686 A | 11/2002 |
| WO | WO 02/089686 | 11/2002 |
| WO | 02100459 A | 12/2002 |
| WO | WO 02/100459 | 12/2002 |
| WO | 03099382 A | 12/2003 |
| WO | WO 03/099382 | 12/2003 |
| WO | 2004037341 | 5/2004 |
| WO | 2005065284 A | 7/2005 |
| WO | 2009134876 A | 11/2009 |
| WO | 2010118387 A1 | 10/2010 |
| WO | 2010151277 A | 12/2010 |
| WO | 2011047387 A | 4/2011 |
| WO | 2012071526 A | 5/2012 |
| WO | 2012088149 A | 6/2012 |

OTHER PUBLICATIONS

Davalos, R.V. et al., 2005, "Tissue ablation with irreversible electroporation." Annals of Biomedical Engineering, 3 (2):223-231.

Edd, J.F, et al., 2007, "Mathematical modeling of irreversible electroporation for treatment planning.", Technology in Cancer Research and Treatment., 6:275-286.

Garcia et al., "Irreversible electroporation (IRE) to treat brain cancer." ASME Summer Bioengineering Conference, Marco Island, FL, Jun. 25-29, 2008.

PCT International Preliminary Report on Patentability for PCT/US2009/042100, dated Nov. 2, 2010 (7 pages).

(56) References Cited

OTHER PUBLICATIONS

PCT International Search Report for PCT/US2009/042100, dated Jul. 9, 2009 (1 page).
Bolland, F., et al., "Development and chracterisation of full-thickness acellular porcine bladder matrix for tissue engineering", Biomaterials, Elsevier Science Publishers, Barking, GB, vol. 28, No. 6, Nov. 28, 2006, pp. 1061-1070.
Co-pending U.S. Appl. No. 10/571,162, filed Oct. 18, 2006 (published as 2007/0043345 on Feb. 22, 2007).
Extended European Search Report. May 11, 2012. PCT/US2009042100.
Gilbert, T. W., et al., "Decellularization of tissue and organs", Biomaterials, Elsevier Science Publishers, Barking, GB, vol. 27, No. 19, Jul. 1, 2006, pp. 3675-3683.
Maor et al., The Effect of Irreversible Electroporation on Blood Vessels, Tech. in Cancer Res. and Treatment, vol. 6, No. 4, Aug. 2007, pp. 307-312.
Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.
PCT International Preliminary Report on Patentability for PCT/US09/62806, dated Jan. 4, 2012, 6pgs.
PCT International Search Report (Aug. 2, 2011), Written Opinion (Aug. 2, 2011), and International Preliminary Report on Patentability (Apr. 17, 2012) of PCT/US10/53077.
PCT International Search Report (Jul. 9, 2009), Written Opinion (Jul. 9, 2009), and International Preliminary Report on Patentability (Nov. 2, 2010) of PCT/US2009/042100.
Rubinsky, B., "Irreversible Electroporation in Medicine", Technology in Cancer Research and Treatment, vol. 6, No. 4, Aug. 1, 2007, pp. 255-259.
Sano, M. B., et al., "Towards the creation of decellularized organ constructs using irreversible electroportion and active mechanical perfusion", Biomedical Engineering Online, Biomed Central LTD, London, GB, vol. 9, No. 1, Dec. 10, 2010, p. 83.
Co-Pending U.S. Appl. No. 13/550,307, filed Jul. 16, 2012.
Maor, E., A. Ivorra, and B. Rubinsky, Non Thermal Irreversible Electroporation: Novel Technology for Vascular Smooth Muscle Cells Ablation, PLoS ONE, 2009, 4(3): p. e4757.
Maor, E., A. Ivorra, J. Leor, and B. Rubinsky, Irreversible electroporation attenuates neointimal formation after angioplasty, IEEE Trans Biomed Eng, Sep. 2008, 55(9): p. 2268-74.
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
PCT International Search Report (Aug. 22, 2012), and Written Opinion (Aug. 22, 2012) of PCT/US11/66239.
PCT International Search Report and Written Opinion (Jul. 25, 2012) of PCT/US2011/062067.
Rajagopal, V. and S.G. Rockson, Coronary restenosis: a review of mechanisms and management, The American Journal of Medicine, 2003, 115(7): p. 547-553.
Co-pending U.S. Appl. No. 12/432,295 (published as 2009/0269317).
Co-pending U.S. Appl. No. 12/491,151 (published as 2010/0030211).
Co-pending U.S. Appl. No. 12/609,779, filed Oct. 30, 2009.
Co-pending U.S. Appl. No. 10/571,162 (published as 2007/0043345).
Baker, et al., Calcium-Dependent Exocytosis in Bovine Adrenal Medullary Cells with Leaky Plasma Membranes, *Nature*, vol. 276, pp. 620-622, 1978.
Beebe, S.J., et al., Nanosecond pulsed electric field (nsPEF) effects on cells and tissues: apoptosis induction and tumor growth inhibition. PPPS-2001 Pulsed Power Plasma Science 2001, 28$^{th}$ IEEE International Conference on Plasma Science and 13$^{th}$ IEEE International Pulsed Power Conference, Digest of Technical Papers (Cat. No. 01CH37251). IEEE, Part vol. 1, 2001, pp. 211-215, vol. I, Piscataway, NJ, USA.
Bown, S.G., Phototherapy of tumors. *World J. Surgery*, 1983. 7: p. 700-9.
BPH Management Strategies: Improving Patient Satisfaction, *Urology Times*, May 2001, vol. 29, Supplement 1.
Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.
Coates, C.W.,et al., "The Electrical Discharge of the Electric Eel, Electrophorous Electricus," Zoologica, 1937, 22(1), pp. 1-32.
Cowley, Good News for Boomers, *Newsweek*, Dec. 30, 1996/Jan. 6, 1997.
Cox, et al., Surgical Treatment of Atrial Fibrillation: A Review, *Europace* (2004) 5, S20-S-29.
Davalos, et al ., Theoretical Analysis of the Thermal Effects During in Vivo Tissue Electroporation, Bioelectrochemistry, vol. 61, pp. 99-107, 2003.
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.
Dev, et al., Sustained Local Delivery of Heparin to the Rabbit Arterial Wall with an Electroporation Catheter, *Catheterization and Cardiovascular Diagnosis*, Nov. 1998, vol. 45, No. 3, pp. 337-343.
Edd, J., et al., In-Vivo Results of a New Focal Tissue Ablation Technique: Irreversible Electroporaton, *IEEE Trans. Biomed. Eng.* 53 (2006) p. 1409-1415.
Foster, R.S., et al., High-intensity focused ultrasound in the treatment of prostatic disease. *Eur. Urol.*, 1993. 23: 44-7).
Gauger, et al., A Study of Dielectric Membrane Breakdown in the Fucus Egg, *J. Membrane Biol*, vol. 48, No. 3, pp. 249-264, 1979.
Gilbert, et al., The Use of Ultrasound Imaging for Monitoring Cryosurgery, Proceedings 6$^{th}$ Annual Conference, IEEE Engineering in Medicine and Biology, 107-111, 1984.
Huang, et al., Micro-Electroporation: Improving the Efficiency and Understanding of Electrical Permeabilization of Cells, *Biomedical Microdevices*, vol. 2, pp. 145-150, 1999.
Issa, et al., The TUNA Procedure for BPH: Review of the Technology: The TUNA Procedure for BPH: Basic Procedure and Clinical Results, Reprinted from *Infections in Urology*, Jul./Aug. 1998 and Sep./Oct. 1998.
Miller, L., et al., Cancer cells ablation with irreversible electroporation, *Technology in Cancer Research and Treatment* 4 (2005) 699-706.
Mir, Therapeutic Perspectives of in Vivo Cell Electropermeabilization, *Bioelectrochemistry*, vol. 53, pp. 1-10, 2000.
Mir, L.M., et al., Electric Pulse-Mediated Gene Delivery to Various Animal Tissues, in Advances in Genetics, Academic Press, 2005, p. 83-114.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.
Naslund, Michael J., Transurethral Needle Ablation of the Prostate, *Urology*, vol. 50, No. 2, Aug. 1997.
Naslund, Cost-Effectiveness of Minimally Invasive Treatments and Transurethral Resection (TURP) in Benign Prostatic Hyperplasia (BPH), (Abstract), Presented at 2001 AUA National Meeting, Anaheim, CA, Jun. 5, 2001.
Neumann, et al., Gene Transfer into Mouse Lyoma Cells by Electroporation in High Electric Fields, *J. Embo.*, vol. 1, No. 7, pp. 841-845, 1982.
Onik, et al., Sonographic Monitoring of Hepatic Cryosurgery in an Experimental Animal Model, *AJR American J. of Roentgenology*, vol. 144, pp. 1043-1047, May 1985.
Onik, et al., Ultrasonic Characteristics of Frozen Liver, *Cryobiology*, vol. 21, pp. 321-328, 1984.
Organ, L.W., Electrophysiological principles of radiofrequency lesion making, *Apply. Neurophysiol.*, 1976. 39: p. 69-76.
Piñnero, et al., Apoptotic and Necrotic Cell Death Are Both Induced by Electroporation in HL60 Human Promyeloid Leukaemia Cells, *Apoptosis*, vol, 2, No. 3, 330-336, Aug. 1997.

(56) References Cited

OTHER PUBLICATIONS

Rols, M.P., et al., Highly Efficient Transfection of Mammalian Cells by Electric Field Pulses: Application to Large Volumes Of Cell Culture by Using a Flow System, Eur. J. Biochem. 1992, 206, pp. 115-121.
Rubinsky, B., ed, Cryosurgery. *Annu Rev. Biomed*. Eng. vol. 2 2000. 157-187.
Shiina, S., et al, Percutaneous ethanol injection therapy for hepatocellular carcinoma: results in 146 patients. *AJR*, 1993, 160: p. 1023-8.
Thompson, et al., To determine whether the temperature of 2% lignocaine gel affects the initial discomfort which may be associated with its instillation into the male urethra, *BJU International* (1999), 84, 1035-1037.
Weaver, et al., Theory of Electroporation: A Review, *Bioelectrochemistry and Bioenergetics*, vol. 41, pp. 136-160, 1996.
Zlotta, et al., Possible Mechanisms of Action of Transurethral Needle Ablation of the Prostate on Benign Prostatic Hyperplasia Symptoms: a Neurohistochemical Study, Reprinted from *Journal of Urology*, vol. 157, No. 3, Mar. 1997, pp. 894-899.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.
Amasha et al., Clin Phys. Physiol Meas, 9:49-53 (1988).
Andreason (1993) J. Tiss. Cult. Meth. 15:56-62.
Barber (1993) Advances in Biomedical Engineering, pp. 165-173.
Beneken and Thevenia (eds) IOS Press pp. 165-173 (1993).
Blad et al., Physiol Meas., 17:A105-A115 (1996).
Brown et al., Clin Phys Physiol Meas, 13:175-179 (1992).
Cook et al. (Aug. 1994) IEEE Transactions on Biomedical Engineering, 41(6):713-722.
Crowly, Biophysical Journal, 13:711-724 (1973).
Davalos et al., IEEE Transactions on Biomedical Engineering, 49(4):400-403 (Apr. 2002).
Davalos et al., Annals of Biomedical Engineering 33(2):223-231 (Feb. 2005).
Dean et al., Am. J. Physiol. Cell Physiol., 289:233-235 (2005).
Dev et al., IEEE Transactions of Plasma Science, 28(1):206-223 (Feb. 2000).
Duraiswami et al., (1998) Engineering and Analysis with Boundary Elements, 22:13-31.
Duraiswami et al. (1997) Chemical Engineering Science, 32(13:2185-2196.
Duraiswami et al. (1997) Boundary Element Technology XII, pp. 226-237.
Erez et al., J. Biomech. Eng., 102(1):42-9 (1980).
Fox et al. (May 1997), Sampling Conductivity Images Via MCMC, Mathematics Department, Auckland University, New Zealand.
Gehl et al., Biochimica et Biophysica Acta, 1428:233-240 (1999).
Gencer et al. (Feb. 1996) Transactions on Biomedical Engineering, 43(2):139-149.
Gilbert et al. (1997), Biochimica et Biophysica Act, 1334:9-14.
Gothelf et al., Cancer Treatment Reviews, 29:371-387 (2003).
Griffiths et al. (Oct. 1989) Phys. Med. Biol., 34(10):1465-1476.
Griffiths et al. (1995), IEEE Transactions on Biomedical Engineering, 42:948-954.
Griffiths et al. (1987) Phys. Med. Biol., 32(11):1435-1444 (1987).
Glidewell et al., (1993) Biomed Sci Instrum, 29:251-257.
Gumerov et al. (Jun. 1999) 13th International Conference on Boundary Element Technology, BETECH, Las Vegas Nevada.
Hapala (1997) Critical Reviews in Biotechnology, 17:105-122.
Heller et al. (1999) Advanced Drug Delivery Reviews, 35:119-129.
Ho et al. (1996) Critical Reviews in Biotechnology 16:349-362.
Holder et al. (1997) Proceedings of the X. International Conference on Electrical Bioimpedance, pp. 512-519.
Hughes et al. (1994) Physiol Meas, 15:A199-A209.
Ivanusa et al., Radiol Oncol., 35(2):139-147 (2001).
Jaroszeski et al. (1999) Advanced Drug Delivery Reviews 35:131-137.
Kinosita et al., PNAS, 74(5):1923-1927 (May 1977).
Liu et al. (1992) Clin Phys Physiol Meas 13(Supp. A):197-200.
Lurquin (1997) Molecular Biotechnology, 7:5-35.
Lundqvist et al. (1998) Proc Natl Acad Sci USA, 95:10356-10360.
Lynn et al., J. Gen. Physiol, 26:179-93 (1942).
Miklavcic et al., Biophysical Journal, 74:2152-2158 (May 1998).
Miklavcic et al., Biochimica et Biophysica Acta, 1523:73-83(2000).
Mir et at (1991) C.R. Acad Sci Paris, 313(III):613-618.
Mir et al., European Journal of Cancer, 27:68-72 (1991).
Mir et al., British Journal of Cancer, 77(12):2336-2342 (1998).
Narayan et al. (1992) J. Urol., 148:1600-1604.
Neumann et al., J. Membrane Biol., 10:279-290 (1972).
Okino et al., Japanese Journal of Cancer Resesarch, 78(12):1319-21 (1987).
Schmuckler (1994) Engineering in Medicine and Biology Society, Engineering Advances: New Opportunities for Biomedical Engineers, Proceedings of the 16th Annual Internal Conference of the IEEE, vol. 1, p. A74.
Sersa et al., Br. J. Cancer, 87(9):1047-54 (2002).
Sersa et al., Oncol., 37(1):43-8 (2003).
Sharma et al (1996) Biophysical Journal, vol. 71:3229-3241.
Weaver (1993) Journal of Cellular Biochemistry, 51:426-435.
Zimmerman et al., Biophysical Journal, 14(11):881-889 (1974).
International Search Reports and Written Opinions from PCT/US2010/030629; PCT/U52009/042100; and PCT/US2004/043477.
Co-Pending Application No. PCT/US04/43477, filed Dec. 21, 2004.
Co-Pending Application No. PCT/US09/42100, filed Apr. 29, 2009.
Co-Pending Application No. PCT/US09/62806, filed Oct. 30, 2009.
Co-Pending Application No. PCT/US10/30629, filed Apr. 9, 2010.
Co-Pending Application No. PCT/US11/32067, filed Nov. 23, 2011.
Co-Pending Application No. PCT/US11/66239, filed Dec. 20, 2011.
Co-Pending U.S. Appl. No. 13/332,133, filed Dec. 20, 2011.
Mir et al., "Mechanisms of Electrochemotherapy" Advanced Drug Delivery Reviews 35:107-118 (1999).
PCT International Search Report (Jul. 15, 2010), Written Opinion (Jul. 15, 2010), and International Preliminary Report on Patentability (Oct. 11, 2011) from PCT/US2010/030629.
PCT International Search Report, 4 pgs, (Jul. 30, 2010), Written Opinion, 7 pgs, (Jul. 30, 2010), and International Preliminary Report on Patentability, 8 pgs, (Oct. 4, 2011) from PCT/US2010/029243.
PCT Written Opinion for PCT/US09/62806, dated Jan. 10, 2010, 5pgs.
Precision Office TUNA System, When Patient Satisfaction is Your Goal, 2001.
Vidamed, Inc., Transurethral Needle Ablation (TUNA): Highlights from Worldwide Clinical Studies, Vidamed's Office TUNA System, 2001.
Boone, K., Barber, D. & Brown, B. Review—Imaging with electricity: report of the European Concerted Action on Impedance Tomography. J. Med. Eng. Technol. 21, 201-232 (1997).
Davalos, R. V. & Rubinsky, B. Temperature considerations during irreversible electroporation. International Journal of Heat and Mass Transfer 51, 5617-5622, doi:10.1016/j.ijheatmasstransfer.2008.04. 046 (2008).
Garcia, P. et al. Intracranial nonthermal irreversible electroporation: in vivo analysis. J Membr Biol 236, 127-136 (2010).
International Preliminary Report on Patentability of Corresponding International Application No. PCT/2011/062067, dated May 28, 2013.
International Preliminary Report on Patentability of Corresponding International Application No. PCT/2011/066239, dated Jun. 25, 2013
Jossinet et al., Electrical Impedance Endo-Tomography: Imaging Tissue From Inside, IEEE Transactions on Medical Imaging, vol. 21, No. 6, Jun. 2002, pp. 560-565.
Lee, E. W. et al. Advanced Hepatic Ablation Technique for Creating Complete Cell Death : Irreversible Electroporation. Radiology 255, 426-433, doi:10.1148/radiol.10090337 (2010).
Pavselj, N. et al. The course of tissue permeabilization studied on a mathematical model of a subcutaneous tumor in small animals. IEEE Trans Biomed Eng 52, 1373-1381 (2005).
Phillips, M., Maor, E. & Rubinsky, B. Non-Thermal Irreversible Electroporation for Tissue Decellularization. J. Biomech. Eng, doi:10.1115/1.4001882 (2010).

(56) References Cited

OTHER PUBLICATIONS

Sel, D. et al. Sequential finite element model of tissue electropermeabilization. IEEE Transactions on Biomedical Engineering 52, 816-827, doi:10.1109/tbme.2005.845212 (2005).
Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).
Weaver, J. C., Electroporation of biological membranes from multicellular to nano scales, IEEE Trns. Dielectr. Electr. Insul. 10, 754-768 (2003).
Co-Pending U.S. Appl. No. 12/906,923, Response to Restriction Requirement, dated Mar. 19, 2014, 3 pages.
Agerholm-Larsen, B., et al., "Preclinical Validation of Electrochemotherapy as an Effective Treatment for Brain Tumors", Cancer Research 71: 3753-3762 (2011).
Appelbaum, L., et al., "US Findings after Irreversible Electroporation Ablation: Radiologic-Pathologic Correlation" Radiology 262(1), 117-125 (2012).
Arena, Christopher B., et al., "Towards the development of latent heat storage electrodes for electroporation-based therapies", Applied Physics Letters, 101, 083902 (2012).
Arena, Christopher B., et al.,"Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.
Bagla, S. and Papadouris, D., "Percutaneous Irreversible Electroporation of Surgically Unresectable Pancreatic Cancer: A Case Report" J. Vascular Int. Radiol. 23(1), 142-145 (2012).
Bancroft, et al., Design of a Flow Perfusion Bioreactor System for Bone Tissue-Engineering Applications, Tissue Engineering, vol. 9, No. 3, 2003, p. 549-554.
Ben-David, E.,et al., "Characterization of Irreversible Electroporation Ablation in In Vivo Procine Liver" Am. J. Roentgenol. 198(1), W62-W68 (2012).
Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).
Co-Pending U.S. Appl. No. 12/906,923, filed Oct. 18, 2010.
Co-Pending U.S. Appl. No. 12/906,923, Requirement for Restriction/Election, dated Jan. 29, 2014, 9 pages.
Co-Pending Application No. PCT/US10/53077, filed Oct. 18, 2010.
Co-Pending Application No. PCT/US11/62067, filed Nov. 23, 2011.
Co-Pending U.S. Appl. No. 13/919,640, filed Jun. 17, 2013.
Co-Pending U.S. Appl. No. 13/958,152, filed Aug. 2, 2013.
Co-Pending U.S. Appl. No. 13/989,175, filed May 23, 2013.
Co-Pending U.S. Appl. No. 14/012,832, filed Aug. 28, 2013.
Co-Pending U.S. Appl. No. 14/017,210, filed Sep. 3, 2013.
Corovic, S., et al., "Analytical and numerical quantification and comparison of the local electric field in the tissue for different electrode configurations," Biomed Eng Online, 6, 2007.
Daud, A.I., et al., "Phase I Trial of Interleukin-12 Plasmid Electroporation in Patients With Metastatic Melanoma," Journal of Clinical Oncology, 26, 5896-5903, Dec. 20, 2008.
Davalos, R.V., et al., "Electrical impedance tomography for imaging tissue electroporation," IEEE Transactions on Biomedical Engineering, 51, 761-767, 2004.
Demirbas, M. F., "Thermal Energy Storage and Phase Change Materials: An Overview" Energy Sources Part B 1(1), 85-95 (2006).
Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).
Faroja, M., et al., "Irreversible Electroporation Ablation: Is the entire Damage Nonthermal?", Radiology, 266(2), 462-470 (2013).

Foster RS, "High-intensity focused ultrasound in the treatment of prostatic disease", European Urology, 1993, vol. 23 Suppl 1, pp. 29-33.
Foster, R.S., et al., Production of Prostatic Lesions in Canines Using Transrectally Administered High-Intensity Focused Ultrasound. Eur. Urol., 1993; 23: 330-336.
Garcia P.A., et al., "7.0-T Magnetic Resonance Imaging Characterization of Acute Blood-Brain-Barrier Disruption Achieved with Intracranial Irreversible Electroporation", PLOS ONE, Nov. 2012, 7:11, e50482.
Garcia P.A., et al., "Pilot study of irreversible electroporation for intracranial surgery", Conf Proc IEEE Eng Med Biol Soc, 2009:6513-6516, 2009.
Garcia PA, Rossmeisl JH, Jr., Neal RE, 2nd, Ellis TL, Davalos RV, "A Parametric Study Delineating Irreversible Electroporation from Thermal Damage Based on a Minimally Invasive Intracranial Procedure", Biomed Eng Online 10: 34 (2011).
Garcia, P. A., et al., "Towards a predictive model of electroporation-based therapies using pre-pulse electrical measurements," Conf Proc IEEE Eng Med Biol Soc, vol. 2012, pp. 2575-2578, 2012.
Garcia, P. A., et al., "Non-thermal Irreversible Electroporation (N-TIRE) and Adjuvant Fractioned Radiotherapeutic Multimodal Therapy for Intracranial Malignant Glioma in a Canine Patient" Technol. Cancer Res. Treatment 10(1), 73-83 (2011).
Hjouj, M., et al., "Electroporation-Induced BBB Disruption and Tissue Damage Depicted by MRI", Neuro-Oncology 13: Issue suppl 3, abstract ET-32 (2011).
Hjouj, M., et al., "MRI Study on Reversible and Irreversible Electroporation Induced Blood Brain Barrier Disruption", PLOS ONE, Aug. 2012, 7:8, e42817.
Lee, E.W., et al., "Imaging guided percutaneous irreversible electroporation: ultrasound and immunohistological correlation", Technol Cancer Res Treat 6: 287-294 (2007).
Li, W., et al., "The Effects of Irreversible Electroporation (IRE) on Nerves" PloS One, Apr. 2011, 6(4), e 18831.
Mahmood, F., et al., "Diffusion-Weighted MRI for Verification of Electroporation-Based Treatments", Journal of Membrane Biology 240: 131-138 (2011).
Mahnic-Kalamiza, S., et al., "Educational application for visualization and analysis of electric field strength in multiple electrode electroporation," BMC Med Educ, vol. 12, p. 102, 2012.
Marty, M., et al., "Electrochemotherapy—An easy, highly effective and safe treatment of cutaneous and subcataneous metastases: Results of ESOPE (European Standard Operating Procedures of Electrochemotherapy) study," European Journal of Cancer Supplements, 4, 3-13, 2006.
Neal II, R. E., et al., "Experimental characterization and numerical modeling of tissue electrical conductivity during pulsed electric fields for irreversible electroporation treatment planning," IEEE Trans Biomed Eng., vol. 59:4, pp. 1076-1085, Epub Jan. 6, 2012.
Neal II, R. E., et al., "Successful Treatment of a Large Soft Tissue Sarcoma with Irreversible Electroporation", Journal of Clinical Oncology, 29:13, e372-e377 (2011).
Rubinsky, B., et al., "Irreversible Electroporation: A New Ablation Modality—Clinical Implications" Technol. Cancer Res. Treatment 6(1), 37-48 (2007).
Salford, L.G., et al., "A new brain tumour therapy combining bleomycin with in vivo electropermeabilization", Biochem. Biophys. Res. Commun., 194(2): 938-942 (1993).
Sharma, A. , et al., "Review on Thermal Energy Storage with Phase Change Materials and Applications", Renewable Sustainable Energy Rev. 13(2), 318-345 (2009).
Thomson, K. R., et al., "Investigation of the Safety of Irreversible Electroporation in Humans" J. Vascular Int. Radiol. 22 (5), 611-621 (2011).
Co-Pending U.S. Appl. No. 13/332,133, Official Non-Final Office Action dated Sep. 4, 2014, 13 pages.
Co-Pending U.S. Appl. No. 12/906,923, Non-Final Office Action dated Oct. 24, 2014, 11 pages.

\* cited by examiner

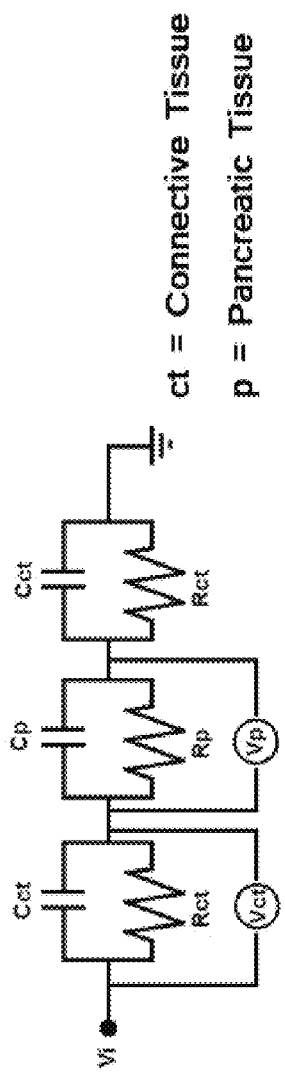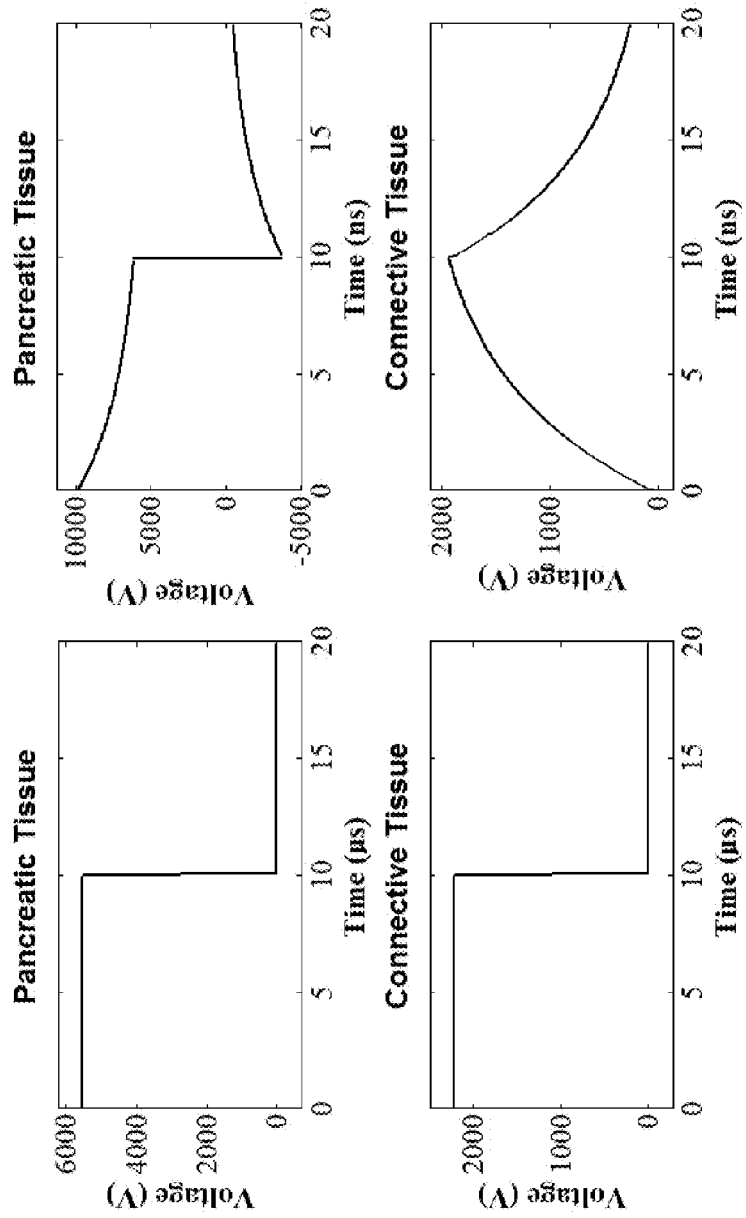
FIG. 3A
FIG. 3B

INTEGRATION OF VERY SHORT ELECTRIC PULSES FOR MINIMALLY TO NONINVASIVE ELECTROPORATION

CROSS-REFERENCE TO RELATED APPLICATIONS

This application relies on and claims the benefit of the filing date of U.S. Provisional Patent Application No. 61/167, 997, filed 9 Apr. 2009, and U.S. Provisional Patent Application No. 61/285,618, filed 11 Dec. 2009, the entire disclosures of both of which are hereby incorporated herein in their entireties.

STATEMENT OF GOVERNMENT INTEREST

This invention was made with government support under Contact CBET-0933335 awarded by National Science Foundation. The government has certain rights in the invention.

BACKGROUND OF THE INVENTION

1. Field of the Invention

The present invention relates to the field of biomedical engineering and medical treatment of diseases and disorders. More specifically, the invention relates to methods for destroying aberrant cells, including tumor tissues, using a series of electrical pulses having durations on the nanosecond scale.

2. Description of Related Art

Treatment of abnormal cell growth in or on normal body tissues and organs can be achieved in many different ways to achieve reduced aberrant cell growth and even destruction of an aberrant cell mass. In general, treatments known in the art involve surgical intervention to physically remove an aberrant cell mass or tissue comprised of tumor cells, radiation to kill aberrant cells, exposure of aberrant cells to toxic chemicals (i.e., chemotherapy), or a combination of two or all three of these. While each treatment modality has shown significant effectiveness in treatment of various cell proliferative diseases, no one technique has been shown to be highly effective at treating all types of cell proliferative diseases and disorders. Furthermore, each technique has significant drawbacks. For example, surgical intervention is highly effective at removal of solid tumors on tissues and organs that are physically accessible and capable of sustaining physical damage or capable of regeneration. However, surgical intervention can be difficult to perform on tumors that are not readily accessible or on organs that do not regenerate, and can involve substantial physical damage to the patient, requiring extensive recuperation times and follow-on treatments. Likewise, treatment with radiation can result in undesirable collateral damage to tissue surrounding the tumor, and can cause long-lasting side-effects, which can lower the quality of life of the patient. Similarly, chemotherapeutic treatments cause systemic damage to the patient, and can result in significant side-effects that might require a long recuperation period or permanent damage to the patient.

Recently, electric pulse therapies, which are initiated by exposing cells or tissues to electric fields, have been studied for cancer treatment in the form of electroporation. In addition to the suffix "poration", the terms "breakdown" and "permeabilization" have been used to characterize this phenomenon, in which the application of certain short direct current (DC) or alternating current (AC) electric fields can result in an increase in the permeability of a cell's plasma membrane and intracellular membranes. As a function of the induced transmembrane potential (the electric potential difference across the plasma membrane), the pulse can have no effect on the plasma membrane, reversibly permeabilize the plasma membrane after which cells can survive (reversible electroporation), or irreversibly permeabilize the plasma membrane in a manner that leads to cell death, presumably through a loss of homeostasis (irreversible electroporation or IRE). It is generally accepted that IRE occurs if the induced transmembrane voltage reaches a value of about one volt at room temperature. In IRE procedures for inducing cell death, the pulse amplitude is typically on the order of hundreds of volts. The pulse duration employed in IRE is longer than the charging time of the plasma membrane, which is typically taken to be around one microsecond. Supra-poration is a type of electroporation that occurs when the electric pulse duration used is in the nanosecond time range, and shorter than the charging time of the plasma membrane of a target cell. When this occurs, cell death is no longer a consequence primarily of irreversible plasma membrane permeabilization. Rather, it is at least partially the result of structural deformation of intracellular organelles. In electroporation, the voltages are applied in order to electroporate tissue without inducing significant Joule heating, which would significantly damage major blood vessels and the extracellular matrix, as well as surrounding healthy tissue. For a specific tissue type and set of pulse conditions, the primary parameter determining the volume that undergoes electroporation is the electric field distribution within the tissue. Typically, electroporation is induced by applying 100 us or 20 ms pulses.

Although advances have been made recently in the use of electric pulses to induce cell death, there still exists a need in the art for improved methods for destroying diseased or disordered tissues, such as tumor tissues. The present invention addresses those needs.

DEFINITIONS

The following terms are to be understood within this document as having the meanings that follow unless the context dictates otherwise:

The term "layer" is to be understood as an epithelial layer, skin, vascular, or other tissue that is designated as not to be disturbed. An epithelial layer is a general tissue type comprised of one or more monolayers of cells in which the cells are connected by tight junctions. Such tissues form linings of organs and other specialized structures. Qualitatively, the main barrier of each monolayer consists of two cell membranes.

The term "membrane" is to be understood as the plasma membrane, which is the lipid bilayer separating the cytoplasm of the cell from the extracellular environment. Alternatively, the "nuclear membrane" or "nuclear envelope" is the double lipid bilayer separating the contents of the nucleus from the cytoplasm of the cell.

Electrochemotherapy (ECT) is the use of membrane permeabilizing electric pulses in combination with cytotoxic drugs.

Electrogenetherapy (EGT) is the use of membrane permeabilizing electric pulses in combination with genes.

Electric pulse therapy is IRE, ECT, EGT, or supraporation, or combination of two or more of these.

SUMMARY OF THE INVENTION

The present invention provides an advancement over tissue ablation techniques previously devised by providing methods for precisely and rapidly killing diseased, damaged, disordered, or otherwise undesirable biological tissues in situ. More specifically, the present invention provides methods comprising electric pulse therapies for ablating target cells and tissues for the treatment of diseases and disorders. Surprisingly, it has been found that the use of ultra-short pulses that have the ability to cause cell death can be effective as a treatment process for aberrant cell growths. The inventors have developed electroporation techniques using nanosecond-scale pulses as a controlled, precise way to destroy aberrant cells of a tissue or organ, without the deleterious side effect of heating the healthy cells in the vicinity of the undesirable cells. In these methods, one or more electrodes are placed within, near, or around the targeted region to deliver a series of high energy electric pulses to promote cell death. The packing of cells within a tissue is largely heterogeneous, and most organs are covered with epithelial cells joined by tight junctions to form a continuous sheet that rests on a layer of fibrous connective tissue. Further, organs can contain multiple sites of epithelial cells within underlying layers of tissue, for example, the cells forming the lining of ducts. Tight junctions are the preferred sites for electroporation when microsecond-scale pulses longer than the charging time of the membrane are employed, because current is confined to the extracellular space once the surrounding cell membranes are fully charged. Therefore, the voltage drop and resulting electric field is larger across layers of tissue containing tight junctions where current pathways are reduced. This, in turn, reduces the amount of underlying tissue that can be treated. The epithelial layer acts as a shield, absorbing a majority of the voltage drop. This problem can be alleviated through the use of electric pulses with durations shorter than the charging time of plasma membranes, such as on the order of about 1-1,000 nanoseconds. Then it is possible for the field to reach the underlying layers of tissue, because current can flow through both the extracellular and intracellular spaces. All cells present in the organ, regardless of their packing, experience a homogenous electric field distribution. It is advantageous to tune the pattern of pulse delivery to the tissue of interest. Depending on electrode and tissue geometry, pulses can be "stacked" in a monopolar or bipolar train, and individual pulses within each train can be delivered from different electrodes, such that cell death only occurs in targeted regions where the integration of pulses both temporally and spatially yields electroporation. The present disclosure documents how electroporation can effectively be done with nanosecond pulses using a series of pulses (applied from differing electrode pairs or the same set).

The advantages of electric pulse therapies over other ablation techniques lay within their ability to kill tissue through a non-thermal mechanism. The methods of the invention use electroporation to kill target cells while preserving the extracellular matrix, nerves, major blood vessels, and other sensitive structures of the treated tissues, enhancing treatment outcome. Furthermore, the ablation area can be predicted using numerical modeling for accurate treatment planning, and application of the procedure can be monitored in real-time using ultrasound and confirmed with both ultrasound and MRI, among other imaging techniques. The methods of the invention allow for killing of target cells and tissues, and exhibit rapid lesion creation and resolution, prompting the repopulation of the region with healthy cells. Though treatment success is not dependent upon the immune system, a tumor specific immune response capable of helping to destroy any residual micro-metastases occurs when the invention is practiced to kill tumor cells, decreasing the chances of recurrence.

The physical properties of biological tissue vary greatly in response to changes in pulse duration and the differences between electroporation protocols that target either the plasma or nuclear membrane can have a significant influence on the mechanism electric field-tissue interaction. The dielectric permittivity and conductivity of a given tissue are typically functions of frequency, which can be correlated to pulse duration. At varying frequencies, different mechanisms of charge transfer contribute differently to the permittivity and conductivity. Further, most tissues are heterogeneous and exhibit multiple mechanisms of charge transfer. However, because the invention uses pulses at durations shorter than the charging time of a plasma membrane, the electric field distribution within heterogeneous tissue resembles that of homogeneous tissue (discussed in more detail below). Therefore, electroporation protocols according to the invention have the ability to penetrate tissues with a relatively high permittivity, such as connective tissue comprising the outer layer of various organs, such as the pancreas, and bone, and brain. Exemplary embodiments of the present invention include methods to treat pancreatic cancer, leukemia, and brain cancer.

According to the present invention, electric pulse therapies are minimally invasive or non-invasive surgical techniques to ablate undesirable tissue, for example, tumor tissue. The techniques are easy to apply, can be monitored and controlled, are not affected by local blood flow, and do not require the use of adjuvant drugs. Electrogenetherapy (EGT) and Electrochemotherapy (ECT) are similar techniques that are conducted in the presence of genes or drugs, respectively. Because the methods of the invention involve ultra-short electric pulses, the amount of heat generated by the methods of the invention is minimal, and the methods substantially or completely avoid thermal killing of cells. Therefore, the death of healthy, non-target cells by thermal means in the region surrounding aberrant cells being treated is also reduced.

In a first general aspect, the present invention provides a method for treating aberrant cell growth in animals, including humans. Broadly speaking, the method comprises placing one or more electrodes in, around, or near aberrant cells to be destroyed, and causing the electrode(s) to provide an electrical charge to the target aberrant cells through multiple ultra-short electric pulses, resulting in cell death of the aberrant cells. In embodiments, the method comprises placing one or more electrodes into or immediately adjacent to regions of pre-selected aberrant cells within the body of a subject, and causing the electrodes to provide a cell-killing electrical charge to the target cells through multiple ultra-short electric pulses. Depending on the duty cycle at which the pulses are applied, the targeted membrane for charge buildup can be either the plasma or nuclear membrane. Therefore, in embodiments, the method is a method of IRE, and in other embodiments, the method is a method of supra-poration or IRE and supra-poration. The step of placing can be any action that results in an electrically conducting portion of the electrode being reversibly implanted into or set externally around the body tissue of the subject being treated. It thus may be by way of physical placement of an electrode using sufficient force (human or mechanical) to puncture a tissue wall (e.g., skin, pericardium, pleural sac) and implant the electrode at a desired site, or mechanically compress the tissue wall without puncture and place the electrode noninvasively around the desired site.

According to the method of treating, the electrode(s) may represent a complete device for use in the method, or may comprise a portion of a device. Where the electrode comprises a portion of a device, the device can include one or more other elements that are advantageous for delivery of electrical pulses to desired cells. For example, in embodiments the device can include, in addition to electrode(s), a non-conductive sheath or covering that can cover some or all of the electrode(s) during insertion or removal from the subject's body. As such, the sheath can be partially of fully retractable from the electrode. In addition or alternatively, the device can comprise a tip that can assist in implanting the device into tissue of the subject. Various other elements for use in insertion, removal, and use of electrodes in electroporation of tissue in situ can be included, and the practitioner is free to select those desired depending on the particular use contemplated.

In some embodiments, two or more electrodes are used to treat aberrant cell growth and effect cell death. The electrodes may be present on the same or different devices for delivering electrical pulses. Preferably, the parameters for electroporation are selected to minimize or avoid excessive heating of the treated tissue and surrounding tissue, thus reducing collateral damage to healthy tissue near the aberrant cell region. In some embodiments, discussed in more detail below, energized electrodes are distributed outside and about/around a subject and the grounded electrode is placed directly into the region where cells to be treated are found. In other embodiments, no ground electrode is necessary, making the entire procedure completely noninvasive.

The step of providing an electric charge involves applying an appropriate series of electrical pulses to the cells to be treated, where the pulses are characterized by being of relatively high voltage and relatively short duration. According to the invention, the electrical pulses have a duration that is less than the charging time of plasma membranes and have a voltage that is sufficient for cell killing but not so high as to cause substantial killing of surrounding, non-target, healthy cells by thermal heating. Because the method of treating can be applied to numerous cells, tissues, and organs, the precise pulse duration and voltage will vary depending on the particular application. However, pulse lengths in general are on the nanosecond range and voltages are at least about 500 V. Further guidance on selecting parameters is provided below.

The method of treating can be considered a method of treating an animal (including a human) having an aberrant cell growth or mass in or on a tissue or an organ. In exemplary embodiments, the organ is pancreas, brain, bone, heart, or any other organ where electrode puncture of the tissue or tissue heterogeneities limit the extent and predictability of conventional IRE or supra-poration treatment. Under this view, the method can be a method of treating an animal suffering from a disease or disorder resulting from aberrant cell growth by reducing or eliminating some or all of a region of aberrant cells (e.g., tumor). The method can also be a method of treating an animal suffering from a disease or disorder characterized by cell cycle dysfunctions, including cells that are not dying or undergoing apoptotic mechanisms of cell death or similar programmed cell death at appropriate, natural, or naturally induced times, such as those mediated through protein bindings or intracellular cascades. Likewise, the method can be a method of treating an animal suffering from a disease or disorder involving cells with alterations that allow for immune system evasion or immune system indifference.

It thus should be apparent that the present invention provides a method of treating a subject suffering from an aberrant cell growth, where the method comprises: implanting an electrode into or adjacent the aberrant growth region within the body of a subject, and causing multiple electrical pulses to be emitted from the electrode into the aberrant growth region in ten microsecond or shorter pulses to cause predominantly non-thermal killing of aberrantly growing cells by IRE. In embodiments, the method uses pulses of between about 10,000 nanoseconds and about 1 picosecond. Two or more electrodes can be used in the method and can be provided as part of a single device. In some embodiments, the method includes positioning the electrodes at a distance apart from each other to create custom treatment area shapes through varying electrode activation patterns. The methods of the invention can be used to treat neoplasias, such as leukemia or pancreatic cancer. The methods can be used to treat human subjects. Further, according to embodiments of the method, two or more electrodes are used, where one electrode is a current input electrode that is implanted in or adjacent an aberrant growth, and another electrode is a current return electrode that is implanted within the body of the subject at a site adjacent to or distant from the aberrant growth region, or is provided external to the subject. Of course, the alternative configuration can be implemented as well, where the implanted electrode is a return electrode and where a current input electrode is implanted within the body of the subject at a site adjacent to or distant from the aberrant growth region, or is provided external to the subject.

In some embodiments, the method results in a reduction in cell proliferation of the aberrant cells. In other embodiments, the method results in a reduction in the size of a tumor. Yet in other embodiments, the method results in ablation of a tumor.

The method can include emitting multiple electric pulses such that the temporal and spatial summation of such pulses results in the generation of an electric field of about 500 V/cm to 2500 V/cm for 10000 microseconds or less to induce IRE. Alternatively, the method can include emitting multiple electric pulses such that the temporal and spatial summation of such pulses results in the generation of an electric field of about 1 kV/cm to 50 kV/cm for 1000 nanoseconds or less to induce supra-poration in addition to IRE. It is to be recognized that, in various embodiments, the individual electric pulses can be monophasic while in other embodiments, the individual electric pulses can be biphasic. In certain preferred embodiments, a train of monophasic pulses is delivered in one direction, followed by a subsequent pulse train of opposite polarity. Depending on the outcome desired, the waveforms or the electric pulses are triangular, square, sinusoidal, exponential, or trapezoidal. Other geometric shapes are contemplated as well. In some embodiments, an electrode is connected to a system for employing electrical impedance tomography (EIT), computer tomography (CT), Magnetic Resonance Imaging (MRI), or ultrasound to image the tissue prior to treatment by applying small alternating currents that themselves do not damage the tissue.

In embodiments, the invention provides a method of treating a subject suffering from an aberrant cell growth, where the method comprises: contacting the subject with a first electrode, placing at least two additional electrodes outside the subject's body at positions that permit electrical charges to be delivered to the aberrant cell growth, and causing multiple electrical pulses to be emitted from one or more of the electrodes into the aberrant growth region in ten microsecond or shorter pulses to cause predominantly non-thermal killing of aberrantly growing cells by IRE. In certain embodiments, the step of contacting comprises contacting the first electrode with the skin of the subject, while in other embodiments, the step of contacting comprises implanting the first electrode at a site in the subject's body that is adjacent to the aberrant cell growth. Other embodiments contemplate different means of contacting, which will be evident to those of skill in the art without the need to list them herein.

The method can be considered to be a method of delivering an electric pulse through a layer using short pulses. For example, the layer can be bone, muscle, fat, connective tissue, nervous tissue, an endothelial layer, or any other layer present in a subject to be treated. According to some embodiments of the method of the invention, electrical pulses induce a combination of both IRE and supra-poration.

Yet again, the method of the invention can be considered a method of treating a subject suffering from an aberrant growth, where the method comprises: implanting an electrode into or adjacent the aberrant growth, and causing multiple electrical pulses to be emitted from the electrode into the aberrant growth in ten microsecond or shorter pulses, where the electrical pulses cause reversible electroporation of cells of the aberrant growth and/or cells adjacent the aberrant growth, which results in uptake of bioactive substances into the treated cells.

In another general aspect, devices are provided for carrying out the method of the invention. Broadly speaking, the devices of the invention include one or more electrically conductive elements (i.e., electrodes) that can be used for electroporation induced cell killing of target cells within the body of a subject. In embodiments, the devices comprise one or more electrodes for reversible implantation into a subject and for delivering electrical pulses to target tissues and cells in the subject. In other embodiments, the devices comprise a combination of electrically conductive elements for combined delivery of electrical pulses, where one or more elements is designed for reversible implantation into the subject and one or more of the elements is designed for use external to the subject's body. In exemplary embodiments, the devices comprise at least one electrode for placement into the body of a subject and at least one electrically conductive element for placement outside of a subject, where the multiple elements/electrodes work in conjunction to deliver cell-killing nanosecond pulses to target tissues.

The electrodes and/or devices can be provided in the context of a system for performing electroporation. According to the invention, a system comprises at least one electrode and/or device electrically coupled to a power source. The power source provides electrical power to the electrode(s)/device(s) to achieve IRE or supra-poration of target cells, tissues, and organs. In preferred embodiments, the system also includes one or more control units for controlling voltage and duration of pulses to be applied to the cells, tissues, and organs that are subject to the methods of the invention. In embodiments, the power source and control unit are provided as a single element of the system.

BRIEF DESCRIPTION OF THE DRAWINGS

The accompanying drawings, which are incorporated in and constitute a part of this specification, provide data supporting exemplary embodiments of the invention, and together with the written description, serve to explain certain principles and features of the invention.

FIG. 3 depicts an illustration of the equivalent circuit model of the pancreas in Panel A, and the output is shown in Panel B for the voltage drop across the connective tissue membrane (ct) and pancreatic layer (p) following the application of 10 μs (left) and 10 ns (right) square-wave electric pulses.

DETAILED DESCRIPTION OF VARIOUS EMBODIMENTS OF THE INVENTION

Figure 1:
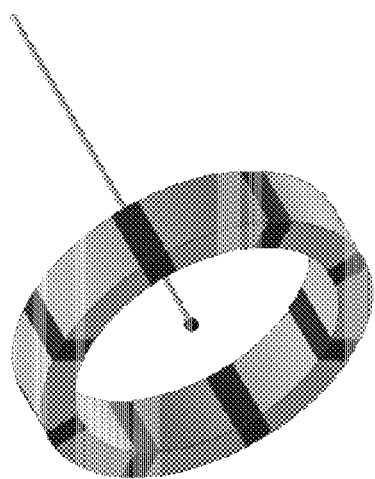
FIG. 1 depicts a representative electrode configuration for treating internal organ tumor regions with pulsed electric fields showing energized (gray) and grounded (black) surfaces.

Reference will now be made in detail to various exemplary embodiments of the invention. It is to be understood that the following discussion of exemplary embodiments is not intended as a limitation on the invention, as broadly disclosed herein. Rather, the following discussion is provided to give the reader a more detailed understanding of certain aspects and features of the invention.

Before embodiments of the present invention are described in detail, it is to be understood that the terminology used herein is for the purpose of describing particular embodiments only, and is not intended to be limiting. Further, where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which the term belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the singular forms "a", "an", and "the" include plural referents unless the context clearly dictates otherwise. Thus, for example, reference to "a pulse" includes a plurality of such pulses and reference to "the sample" includes reference to one or more samples and equivalents thereof known to those skilled in the art, and so forth. Furthermore, the use of terms that can be described using equivalent terms include the use of those equivalent terms. Thus, for example, the use of the term "subject" is to be understood to include the terms "animal", "human", and other terms used in the art to indicate one who is subject to a medical treatment. As another example, the use of the term "neoplastic" is to be understood to include the terms "tumor", "cancer", "aberrant growth", and other terms used in the art to indicate cells that are replicating, proliferating, or remaining alive in an abnormal way.

The present invention provides advancements over currently available tissue ablation techniques by providing improved devices and methods for precisely and rapidly ablating diseased, damaged, disordered, or otherwise undesirable biological tissues in situ. As used herein, the term ablation is used to indicate destruction of cells, but not necessarily destruction of the underlying extracellular matrix. More specifically, the present invention provides new devices and methods for ablating target tissues for the treatment of diseases and disorders, and particularly neoplasias, including both solid tumors and leukemias, by combining ultra-short electric pulses to produce electric field strengths high enough to destabilize cellular membranes. In embodiments relating to IRE, the cellular membranes include the external cell membrane (i.e., plasma membrane). In embodiments relating to supra-poration, the cellular membranes include internal membranes, such as those defining organelles.

Electroporation is a non-thermal, non-linear biophysical mechanism in which the application of an external pulsed electric field leads to an increase in the permeability of cellular membranes. While direct evidence for the exact mechanism of electroporation has yet to be discovered, experiments indicate that the extent of electroporation is attributed to the induced buildup of charge, and consequently, potential difference across the membrane, commonly referred to as the transmembrane potential (TMP). Increasing the TMP has been described to produce various permeabilizing effects on cellular membranes, including those that add to thermal fluctuations within the membrane, wherein the formation of hydrophilic, aqueous pores becomes energetically favorable. The field strength and duration control the onset of permeabilization in the membrane and the extent to which transient permeabilizing defects are allowed to reseal. If the pulse parameters are tuned such that the membrane defects are only temporary, and the cell remains viable, the process is termed reversible electroporation. Reversible electroporation can be used to introduce molecules into cells that, under normal conditions, would not permeate cellular membranes. Reversible electroporation is being studied to facilitate the delivery of anticancer drugs (electrochemotherapy; ECT) and DNA (electrogenetherapy; EGT) into cancer cells through the plasma membrane. There is a narrow window of pulse parameters where ECT and EGT have proven to be effective without reducing cell viability by IRE. IRE results when membrane defects are permanent, leading to cell death presumably through a loss of homeostasis. It is recognized as independent means to destroy substantial volumes of targeted tissue without the use of harmful adjuvant drugs and prior to the onset of thermal injury. Due to its inherent non-thermal nature, IRE promotes preservation of sensitive structures, such as nerves and blood vessel extracellular matrix components. To maintain its non-thermal benefits, the pulse parameters for IRE procedures are restricted to those that minimize any associated Joule heating. The pulse duration employed in IRE is larger than the charging time of the plasma membrane, which is typically on the order of a microsecond. Supra-poration results when the applied pulse is shorter than the charging time of the plasma membrane, and the electric field is able to penetrate the cell. As a result, cell death in supra-poration is induced presumably through damage to intracellular organelles. Because organelles are smaller in diameter than cells, the amplitude required to raise the TMP on organelles up to around 1 V is greater than that in electroporation procedures but, due to the ultra-short nature of the pulses, the accompanying Joule heating is still negligible. While immediate necrosis is suspected as the primary mechanism of cell death following IRE, apoptosis triggered by DNA fragmentation and the release of calcium from intracellular stores occurs in cells exposed to sufficiently high nsPEFs.

Electric pulse therapies are minimally invasive procedures that involve placing electrodes into or around a targeted tissue and delivering a series of short and intense electric pulses in an attempt to localize the treatments to the cancer cells and spare the surrounding healthy cells. When a tumor is located deep within an organ, a minimally invasive needle or catheter based device is needed for the electrodes to reach the tumor. In some instances, the organ puncture required by these designs can, in itself, damage the surrounding healthy cells. For example, even a slight puncture of the pancreas from the insertion of a single needle (0.3 mm diameter) results in widespread cellular injury that may manifest as pancreatitis, which is known to mediate additional postoperative complications. Therefore, treatment of pancreatic cancer and cancers arising in other organs that are sensitive to puncture is limited to the use of non-puncturing plate electrodes placed around the organ. Plate electrodes are best suited to treat tumors lying close to the skin, because of the high potential drop that occurs across epithelial layers, where the field is the largest, limiting the amount of deeper tissue that can be permeabilized without first permeabilizing the overlying layers. Plate electrodes will have a similar problem when placed around organs to treat deep seated tumors, because the energy must be directed through multiple layers of heterogeneous tissue. For example, most organs of the abdominal cavity, including portions of the anterior and inferior surfaces of the pancreas, are covered by the peritoneum. Epithelial cells of the peritoneum are joined by tight junctions to form a continuous sheet that rests on a layer of fibrous connective tissue.

Transport lattice models of multicellular systems have shown that epithelial layers containing tight junctions are preferred sites for electroporation when ECT, EGT, or IRE pulsing protocols are employed. As mentioned, this has to do with the fact that the electrical current associated with pulses longer than around 1000 ns is confined to extracellular spaces prior to the onset of electroporation. When high resistance tight junctions are present, the field is highly concentrated across the cells, because extracellular current pathways are reduced. Further, the extent of electroporation in underlying cells is reduced, because the epithelial layer absorbs a majority of the potential drop. It is possible for the field to reach the underlying cells when ultra-short are employed, because current can flow through both extracellular and intracellular spaces. In this case, all cells present in the organ, regardless of their packing and morphology, experience a homogeneous electric field distribution. Therefore, ultra-short pulses can be delivered to treat hard to reach tumors, or cancer cells that are encapsulated by one or more epithelial layers. When applied in a train, ultra-short pulses can raise the TMP across the plasma membrane above a critical permeabilizing threshold, if each pulse within the train starts before the cell has had time to discharge from the previous pulse.

The effects of integrating multiple, ultra-short pulses on tissue electroporation can be controlled by altering both the electrode type and electrode configuration. As mentioned, it is desirable in some instances to deliver all of the energy from non-puncturing plate electrodes surrounding the target tissue. In this case, the pulses can be delivered in either a monopolar pulse train, where the integration of the pulses serves to raise the TMP to the critical permeabilizing threshold, or a bipolar pulse train, where each pulse within the train can raise the TMP to the critical permeabilizing threshold, and the switch in polarity serves to prevent the charging of epithelial layers and subsequent shielding of underlying layer of tissue. Further, the number of non-puncturing electrodes can be expanded so that each pulse within the train is delivered from a different electrode in attempt to expose only cancer cells in targeted regions to a lethal dose of energy and spare the surrounding healthy cells. The invention also includes the application of ultra-short pulse trains through puncturing energized or grounded electrodes located directly adjacent to or within the targeted tissue. In this case, the electrode configuration can be controlled as before to effectively bypass epithelial layers and ensure homogeneous treatment of innately heterogeneous tissue. Examples describing all designs covered in the claims of the present invention are given subsequently throughout the text.

The present invention describes a method for both inducing supra-poration from low-voltage pulses and inducing IRE from ultra-short pulses. One exemplary basis for the invention is that the temporal and spatial summation of multiple ultra-short, low-voltage pulses can be implemented to construct waveforms that are characteristic of both IRE and supra-poration protocols. This enables the use of IRE for the treatment of inoperable and hard-to-reach cancers, such as pancreatic cancer and leukemia, and makes supra-poration more clinically applicable. It also allows for the use of less invasive electrode designs to improve treatment outcomes.

Despite being a well-known technique, there is significant controversy about the mechanisms governing electroporation and supra-poration. Even though the biophysical phenomenon at the molecular level is not known, the hypothesis is that in the presence of an externally applied electric field, the lipid bilayer in cellular membranes rearranges to create water-filled structures. These structures (or pores) provide a pathway for ions and molecules through the membranes, which normally are impermeable. The dynamics of membrane poration is considered a four-step process: pore induction, expansion, stabilization, and resealing. Initial thermal fluctuations are responsible for the presence of hydrophobic pores. There exists a critical radius where it is more energetically favorable for a hydrophobic pore to transition to a hydrophilic pore. In addition, increasing the transmembrane potential reduces this critical radius and increases the stability of a hydrophilic pore. When the pore reaches this meta-stable state, it becomes permeable to small molecules. The presence of the induced TMP lowers the energy required for the pore's existence. If the transmembrane potential exceeds a critical value, i.e., the breakdown voltage, the hydrophilic pores become unstable and the membrane undergoes irreversible damage, which leads to membrane rupture and subsequent cell death. For most bio-membranes, a transmembrane potential of 1 V is sufficient to induce irreversible membrane breakdown and thus kill the cell. When the electric field has been turned off, the membrane starts to return to its normal membrane potential and resealing of the pores takes place.

In the present invention, the most important parameters for effective electroporation and supra-poration are the electric field strength (pulse amplitude), duration of the field that is applied (pulse length), the total number of pulses that are applied, and the duty cycle and frequency of pulse trains. Electroporation occurs with pulse durations in the microsecond range and electric field amplitudes on the order of hundreds of volts per centimeter. Specifically, for ECT, the field for inducing optimal reversible electroporation conditions is between 300 and 500 V/cm in tumors, when 8 square-wave pulses 100 µs in duration are delivered at a frequency of 1 Hz. For EGT, permeabilization conditions are optimal when 8 square-wave pulses 20 ms in duration are delivered at a frequency of 1 Hz, which constitutes a field of around 90 V/cm.

The tradeoff between pulse amplitude and length is evident in terms of defining the field required to raise TMP to the critical permeabilizing threshold. A similar field strength and duration to those required for ECT can induce IRE when the number of pulses is raised above the traditional 8 pulses to 90 pulses, and the temperature of the tissue remains below 50° C., taken as the threshold for thermal damage. Supra-poration occurs with pulse durations in the nanosecond range and electric field amplitudes on the order of thousands of volts per centimeter. Specifically, electric fields, with strengths in excess of 10 kV/cm and durations as short as 3 ns, can cause electroporation within the membranes of intracellular organelles. As mentioned, because pulse durations employed in supra-poration protocols are shorter than the membrane charging time (around 1 μs), pores are formed in subcellular membranes instead of the plasma membrane. A large variety of other parameters can influence the efficiency of membrane poration, such as the shape of the electrical pulses, polarity, size of target cells, and thermal conditions during and after the pulses.

As mentioned, applied electric pulses alter the transmembrane potential (TMP) of cellular membranes. When membranes are treated as two, spherical, ideal dielectric shells containing and surrounded by a conductive medium, the analytical solution for induced TMP across the plasma membrane and nuclear envelope can be described as a function of time by solving the Laplace equation. Analysis in the frequency domain yields:

$$TMP_{pm}(s) = F_{pm}(\Lambda_n, \Lambda_{ne}, \Lambda_c, \Lambda_{pm}, \Lambda_e) E(s) \cos \theta,$$

$$TMP_{ne}(s) = F_{ne}(\Lambda_n, \Lambda_{ne}, \Lambda_c, \Lambda_{pm}, \Lambda_e) E(s) \cos \theta,$$

where the subscripts n, ne, c, pm, and e describe cellular regions corresponding to the nucleoplasm, nuclear envelop, cytoplasm, plasma membrane, and extracellular space, respectively. The term F represents a transfer function of the TMP that reflects the geometric and dielectric properties of the cellular regions as a function of the complex admittance, which is given by the equation $\Lambda = \sigma + \in s$, where s is the complex frequency. The exact formulation for F is lengthy and is given by Kotnik and Miklavcic (Biophysical Journal, 2006). The term E represents the Laplace transform of the pulsed electric field as a function of time. In some of the following examples, the pulse duration was using a Heaviside step function (ideal rise time) in order to investigate the timescale of complete plasma membrane and nuclear envelope charging and discharging, respectively. In the following examples, the equations were solved and converted back into the time domain by taking the inverse Laplace transform according to, $TMP(t) = L^{-1}[(TMP(s)]$. The properties of the different cellular regions were defined according to the following table:

TABLE 1

| Geometry | Conductivity (S/m) | Relative Permittivity | Dimensions (m) |
|---|---|---|---|
| Conductive Gel | 4 | 80.0 | — |
| Extracellular Space | 0.6 | 80.0 | — |
| Epithelial layer | $2.1 \times 10^{-5}$ | 7.0 | $28.0 \times 10^{-9}$ (thickness) |
| Plasma Membrane | $5.3 \times 10^{-6}$ | 7.0 | $7.0 \times 10^{-9}$ (thickness) |
| Cytoplasm | 0.13 | 60.0 | $10.0 \times 10^{-6}$ (diameter) |
| Nuclear Envelope | $4.3 \times 10^{-3}$ | 22.8 | $40.0 \times 10^{-9}$ (thickness) |
| Nucleoplasm | 0.18 | 120.0 | $5.0 \times 10^{-6}$ (diameter) |

When an electric field is applied across or between two electrodes placed within a homogeneous solution, the field distribution is predicted by the Laplace equation:

$$-\nabla \cdot (\sigma \nabla V) - \varepsilon_o \varepsilon_r \nabla \cdot \left( \frac{\partial \nabla V}{\partial t} \right) = 0$$

where σ and $\in_r$ are the conductivity and relative permittivity, respectively, for a given region. This equation is readily solved by implementing finite-element techniques. The inclusion of a permittivity term accounts for the reactive component of tissue in time dependent pulsing, which is required for obtaining accurate potential distributions in heterogeneous models. Calculations of the TMP across the plasma membrane and nuclear envelope were performed in the following examples by taking the difference between potentials on both sides of the respective membranes.

Both electroporation of the plasma membrane and supra-poration of intracellular membranes are ideal when pulses are applied as to not induce any deleterious thermal effects. However, the differences between the protocols in terms of pulse duration can have a significant influence on the mechanisms of electric field—tissue interaction. The dielectric permittivity and conductivity of a given tissue are typically functions of frequency. At varying frequencies, different mechanisms of charge transfer contribute differently to the permittivity and conductivity. Further, most tissues are heterogeneous and exhibit multiple mechanisms of charge transfer.

Biological tissues are classified as heterogeneous dielectrics, and Maxwell-Wagner effects describe electrical processes at the interface between different dielectrics. There may be free or bound surface charges at the interface, and it is the presence of free charges that is responsible for altering the electric field across the interface. Organs are often compartmentalized, with thin membranes comprising the compartment walls. For example, the lung, the heart, the brain, and the stomach all have multilayer membranes. These membranes have a large influence on current flow, and the ultra-short pulse durations employed in supra-poration protocols can bypass (or electrically short) these membranes, such as the connective tissue capsule surrounding the pancreas, because the pulse duration is shorter than the charging time of the cell membrane, which is defined for a single shell model as:

$$\tau = aC_{pm}\left( \frac{1}{2\sigma_e} + \frac{1}{\sigma_c} \right)$$

where $C_{pm}$), is the capacitance of the membrane, $\sigma_e$, is the conductivity of the external medium, and $\sigma_c$ is the conductivity of the internal medium.

An equivalent circuit model with ideal components (resistors with frequency independent values) can be implemented to describe various interfaces between tissue layers. For the case of three slabs of tissue placed in series between capacitor plates, which mimics noninvasive treatment of pancreatic cancer, the individual tissue components are represented by a parallel combination of a resistor and a capacitor, and the individual components are connected in series to represent the whole organ. The sections in direct contact with the electrodes represent the connective tissue capsule surrounding the pancreas, and the center section is a homogeneous portion of pancreatic tissue. In order to calculate the capacitances and resistances in the circuit model of the pancreas, data on the specific conductivity and relative permittivity of connective tissue and pancreatic tissue is needed. Biological tissue is neither a perfect dielectric nor a perfect conductor, and the values for conductivity and permittivity are dependent upon the frequency of the applied electric field. In electroporation and supra-poration protocols, voltage is delivered to the electrodes in a square pulse waveform, where most of the energy resides at 0 Hz. Therefore, data for connective tissue (estimated to be similar to wet skin) and pancreatic tissue conductivity and permittivity at 0 Hz is used. After applying input voltage of 10 kV as a square pulse waveform for a specified duration, the voltage drop across the connective tissue can be decreased by reducing the pulse duration into the nanosecond time range (see FIG. 3). These results are confirmed by the finite-element solution, as described in FIG. 7. In a similar fashion, a tumor with a higher complex impedance as compared to the surrounding healthy tissue experiences a higher voltage drop when nanosecond pulses are employed, resulting in a targeted electric field therapy.

Figure 4:
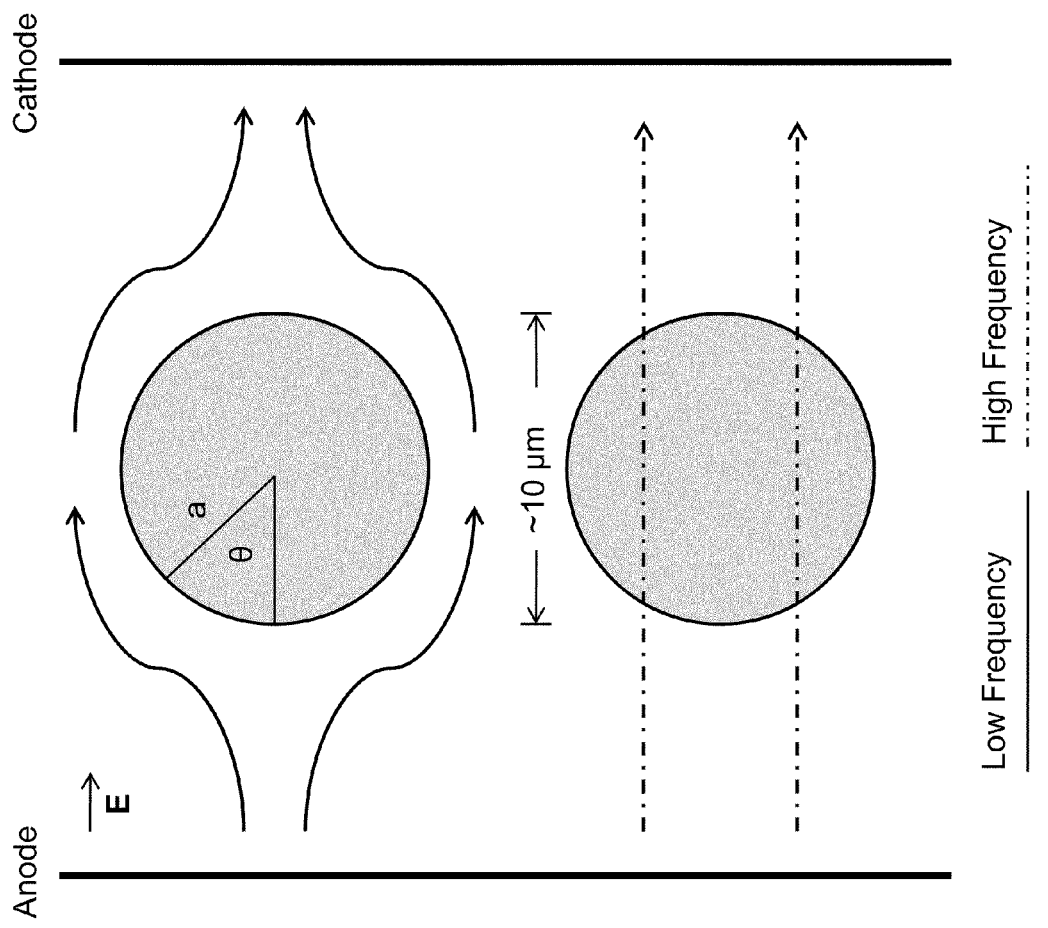
FIG. 4 illustrates the low frequency and high frequency current paths for a volume of cells surrounded by interstitial fluid placed in a uniform electric field.
Figure 10:
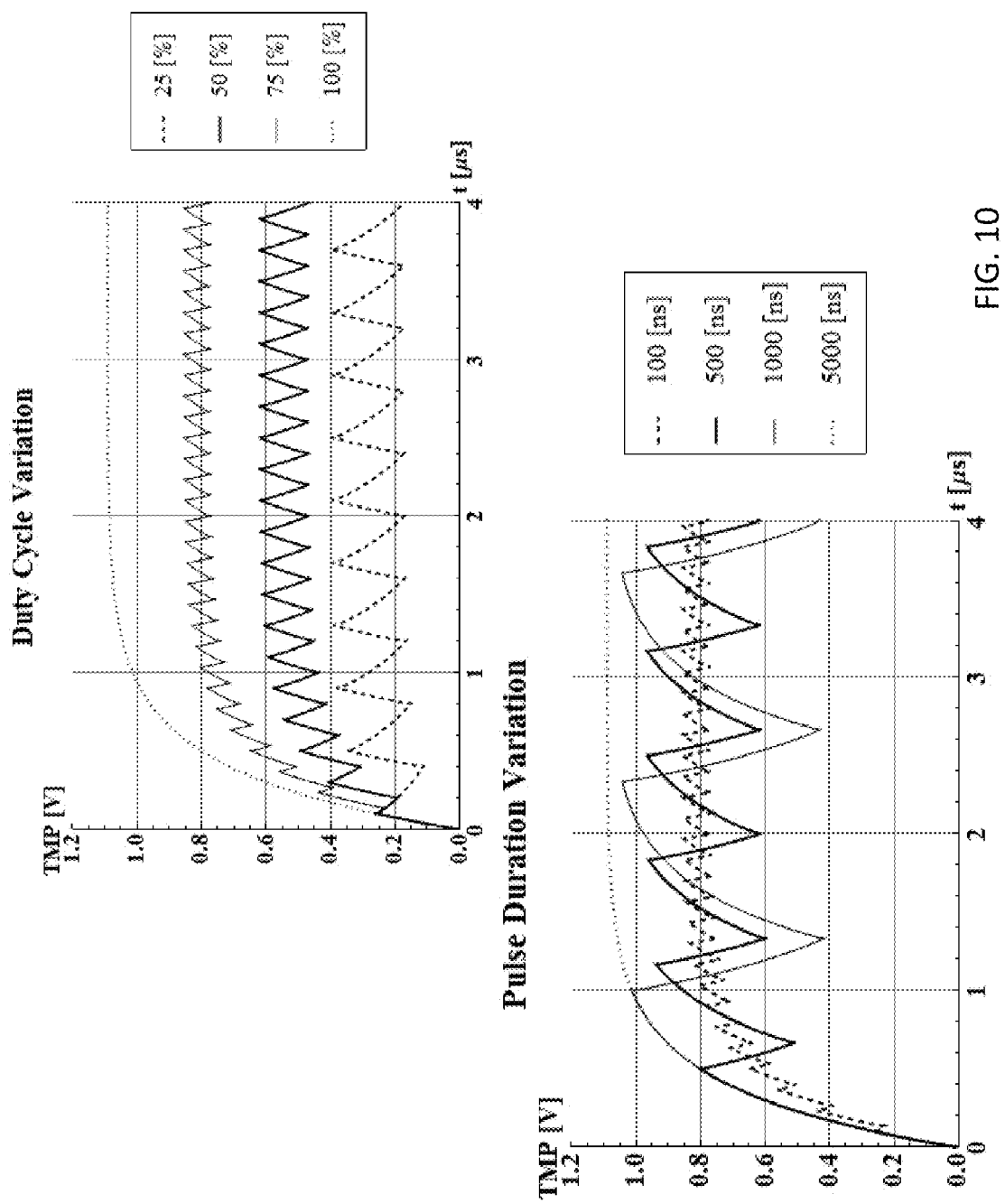
FIG. 10 depicts the results of analytical calculations on transmembrane potential (TMP) for leukemia cells exposed to ultra-short pulse trains of varying duration and duty cycle. In all cases, the applied electric field is 2000 V/cm, and the maximum value of TMP around the cell at the pole is shown. When duty cycle is varied, pulse duration is held constant at 100 ns, and when pulse duration is varied, duty cycle is held constant at 75%.

Electric circuit theory can also be extended to model individual cells, because the wavelength of the pulses in electroporation and supra-poration protocols is evidently much larger than the dimensions of the object of interest. At high frequencies (pulse durations shorter than the charging time of the membrane), current is able to penetrate the cell membrane, which has a high capacitance and low conductivity, and at low frequencies (pulse durations longer than the charging time of the membrane) current tends to travel around the cells (see FIG. 4). As mentioned, in order to take advantage of the ability of ultra-short pulses to bypass tissue heterogeneities in IRE protocols, multiple ultra-short pulses can be combined to generate an electric field capable of inducing a transmembrane potential of 1 V on the plasma membrane of cells. Individual cell responses to electroporation protocols have been assessed with charge-relaxation studies in patch clamp experiments. Additionally, rapid freezing methods have allowed for the characterization of the time sequence of electropores. This information indicates that after approximately 100 ns after the offset of square pulse waveform, the cell membrane begins discharging. Therefore, if multiple ultra-short pulses can be delivered across a cell membrane with less than around 100 ns in between the pulses, then cell can remain polarized long enough for the transmembrane potential to reach 1 V. Specific data on the optimal duty cycle and pulse duration is given in FIG. 10. The analytical solution for the maximum TMP on the plasma membrane of leukemia cells was solved at the pole. As expected, results indicate that as duty cycle is decreased, maximum TMP drops, and the same is true as pulse duration is decreased. However, the induced TMP is less sensitive to changes in pulse duration as compared to changes in duty cycle. Therefore, the pulse generators in the present invention are best suited when operated above a 50% duty cycle at a variety of pulse lengths.

The present invention is distinguishable from conventional electric pulse therapies at least in part in embodiments by the pulse parameters and electrode configurations that are utilized. Trains of pulses are applied in a distinct fashion to induce plasma membrane electroporation. Individual pulses comprising the trains have durations on the order of the charging time of the plasma membrane (nanoseconds) and amplitudes that are characteristic of ECT, EGT, or IRE. This is as opposed to supra-poration, which requires greater amplitudes (~kilovolts) to disrupt intracellular membranes. In embodiments, the temporal and spatial summation of the pulses is such that the TMP on the plasma membrane reaches the critical threshold required for electroporation. This constraint can be met in various ways for the treatment of certain tissues or whole organs. If individual pulses have durations much less than the charging time of the plasma membrane, then multiple pulses must be sequenced to reach the critical TMP. The treatment can then be targeted by delivering each pulse from a different electrode in a custom electrode array placed into or around the desired ablation zone. If individual pulses have durations similar to the charging time of the plasma membrane, then no sequencing is required to reach the critical TMP. However, to treat tissues surrounded by or containing epithelial layers with reduced current pathways, it is still advantageous to apply multiple pulses of alternating polarity to penetrate through these layers and treat the entire volume.

The invention thus encompasses using multiple short electrical pulses to cause killing of target cells by either electroporation or supra-poration. Accordingly, in one aspect, the present invention provides a method of treating targeted aberrant cell growth in a subject. In general, the method includes externally placing or reversibly implanting into a tissue or organ of a subject at least one electrode in proximity to target cells. The electrode(s) may be provided as bare electrically conducting elements, or may be provided as part of a device that includes, among other things, an electrically insulating cover or sheath covering at least a portion of the electrode(s). Once in position, a series of two or more electrical pulses are applied to the target cells in proximity to the electrode(s) to cause cell death as a result of IRE or supra-poration. The electrical pulses are provided as a series of pulses of from 1 picosecond (ps) to 1,000 nanoseconds (ns) or higher (e.g., 10,000 ns) at voltages above about 500 V. The pulses are continued until a desired level of cell killing of target cells is achieved. In embodiments, cell killing is monitored in real-time, although the desired level of cell killing can be accurately predicted beforehand using mathematical modeling on computers. Upon achieving a desired level of cell killing, pulsing is discontinued and the electrode(s) are removed from the treated tissue or organ. Where necessary or desirable, tissue damage due to insertion of the electrode(s) is repaired surgically.

The method of treating according to the invention is, in embodiments, a method of treating a subject suffering from aberrant cell growth in or on a tissue or organ. By aberrant, it is meant that the cells are characterized by the progressive or uncontrolled proliferation of cells that have an abnormality such that they are not regulated properly by normal methods. The method thus can be considered, in embodiments, as a method of treating a disease or disorder involving aberrant cell growth or aberrant failure of cells to die normally. Exemplary embodiments of diseases and disorders are those that affect tissues characterized by relatively high permittivity, such as the outer layer of the pancreas, bone, and the central nervous system, such as the brain and spinal cord. Unlike the present methods, other electroporation methods known in the art are not effective for use on tissues characterized by high permittivity.

Diseases and disorders that can be treated according to the method of the present invention include solid and non-solid tumors, both malignant and benign (generally referred to herein at times as neoplasias). Although the methods of the present invention apply to many different diseases and disorders, exemplary diseases/disorders relate to cancers. Therefore, exemplary embodiments of the present invention are methods that treat cancerous tissues, such as those found in pancreatic cancer, solid bone tumors, leukemia, and brain. Any tumor (or targeted region) can be treated using this technique, although the ideal embodiment is when a less invasive procedure is desired. It is to be understood that, although certain tumors and cancers have been specifically recited herein, the absence of a mention of a particular tumor or cancer type does not imply that the methods are not applicable to that tumor or cancer. Rather, an exhaustive listing of tumors and cancers has not been given because those of skill in the art are fully aware of the various tumors and cancers that can be treated according to the present invention without the need for each to be specifically listed. That is, there are no known tumors or cancers for which the present methods cannot be successfully applied.

Because the methods of the invention can be employed for bony tissue, the methods are particularly well suited for subjects with leukemia. With this disease, cancer of blood-forming stem cells starts in the bone marrow and then spreads to the blood to reach other organs. The current common treatment for leukemia involves autologous stem cell transplantation. In this procedure, stem cells from the subject's own marrow or blood are obtained and engrafted after the patient receives an intense dose of chemotherapy or radiation to kill resident stem and blood cells. The previously removed stem cells are then reintroduced in an attempt to restore hematologic and immunologic function following treatment. There is a high treatment associated mortality rate due to infection prior to engraftment and the toxicity of chemotherapy and radiotherapy. Because the methods of the present invention are minimally invasive, they are preferable for the treatment of leukemia compared to the current treatment.

Regardless of the target cells, tissues, and organs, and regardless of the particular subject involved, the method of the invention includes use of one or more electrodes for placement into or adjacent a site to be treated. Various parameters for localizing electrodes for electroporation in situ are known, for example through the work of the present inventors and their journal publications and patent applications. Those of skill in the art are thus fully capable of locating electrodes for IRE or supra-poration at the appropriate loci for achieving the methods of the present invention. Exemplary parameters are provided below to further assist the practitioner in determining the appropriate placement of electrodes.

According to the methods of the invention, the electric pulses for electroporation and supra-poration are ultra-short, such as in the order of nanoseconds. Surprisingly, it has been found that durations shorter than the charging time of the cell plasma membrane, which is typically taken to be around one microsecond, can be employed in the present invention to successfully cause controlled cell killing. Therefore, durations of the electric pulses include less than 1 microsecond, such as less than 900 nanoseconds, less than 500 nanoseconds, less than 100 nanoseconds, and less than 50 nanoseconds. While no particular lower limit is envisioned, from a practical standpoint, pulse durations of greater than 1 picosecond is the current lower limit, due to device dimensions. Individual picosecond or nanosecond pulses can be combined spatially and temporally to produce a single supra-poration pulse or even an individual IRE pulse. As pulse duration is lowered, a larger number of pulses or a higher voltage per pulse is required to induce IRE or supra-poration.

By reducing the pulse length, larger electric fields can be applied to the treatment area while avoiding thermal damage to non-target tissue (as well as to target tissue). As a result of the decreased pulse length and concomitant reduction in heat production, the methods of the invention allow for treatment of tissues having higher volumes (e.g., larger tumors) than possible if prior art methods were to be employed for in situ treatment of aberrant cell growth. Furthermore, the use of multiple ultra-short pulses allows not only for direct cell killing by way of supra-poration, but also allows for stacking of pulses at a single or multiple electrodes, and delivery of cell killing electrical charges by IRE.

The voltages used in supra-poration according to the present invention are typically higher than those used in IRE, although there may be some overlap in the ranges used for each technique. Voltages used in the methods of the invention range from about 500 V to about 100 kV. As discussed above, any particular voltage value or range of values within this range may be used, and the present disclosure provides for each value and range without the need for each value and range to be specifically recited. The practitioner is free to choose the appropriate voltage, in conjunction with pulse length, that achieves a particular goal.

In embodiments of the method of the present invention, supra-poration or IRE is performed using nanoparticles or small microparticles (i.e., from about 1 nanometer to about 50 micrometers). Use of such small particles can increase the effective treatment area without increasing the applied voltage and resultant thermal damage. Nanoparticles and small microparticles (referred to herein generally as "nanoparticles") offer promising solutions to treat aberrant cell growths because they are of sufficiently small size to enter intercellular spaces and enhance delivery of electrical pulses. The three most important properties of a nanoparticle for enhancing electric fields are its shape, orientation with respect to the applied field, and electrical properties (conductivity and permittivity). In embodiments, the nanoparticles used in the methods of the invention include insulative and conductive nanoparticles of varying shapes. They can enhance the pulsed electric field therapies by lowering the electric field threshold required for inducing supra-poration and enlarging the treatable area. In particular, nanoparticles and electrical conductivity can enhance pulsed electric field therapies by lowering the electric field threshold required for inducing supra-poration. As such, the amount of applied voltage needed to treat an aberrant cell region can be decreased if nanoparticles are employed in the methods.

Further, the nanoparticles can comprise modified surface chemistries to cause the localized destruction of targeted cells, while leaving untargeted cells intact. The selectivity of ultra-short pulsed electric field therapies can be enhanced through the use of nanoparticles that can be functionalized to target specific cancer cells with various antibodies and chemical compounds. These methods can be employed to eliminate a subject of cancer cells within and beyond the treatment margin, while maintaining proper organ function. There are many examples of nanoparticle targeting techniques known in the art. For example, folic acid conjugations can be used to selectively bind to cancer cells with up-regulated folate receptors, such as for breast and brain cancer cells. As another example, antibodies can be conjugated to selectively bind to cancer cells presenting distinct antigens, such as leukemic cells. As a further example, the simple tendency of well suspended nanoparticles (coated with polymers) to diffuse into tumor masses over time following systemic delivery can be employed as a nanoparticle targeting technique. The use of nanoparticles and small microparticles according to the present invention can be based on the concepts disclosed in U.S. patent application Ser. No. 12/609,779, the entire disclosure of which is incorporated herein by reference.

The electric current used in the methods is optionally monitored in real-time and, based on that monitoring, excessive charge delivery is mitigated to reduce damage to healthy tissue. Further, with real-time monitoring, the thermal energy dose can be given such that it is not excessive and damage is reduced to healthy tissue.

Figure 2:
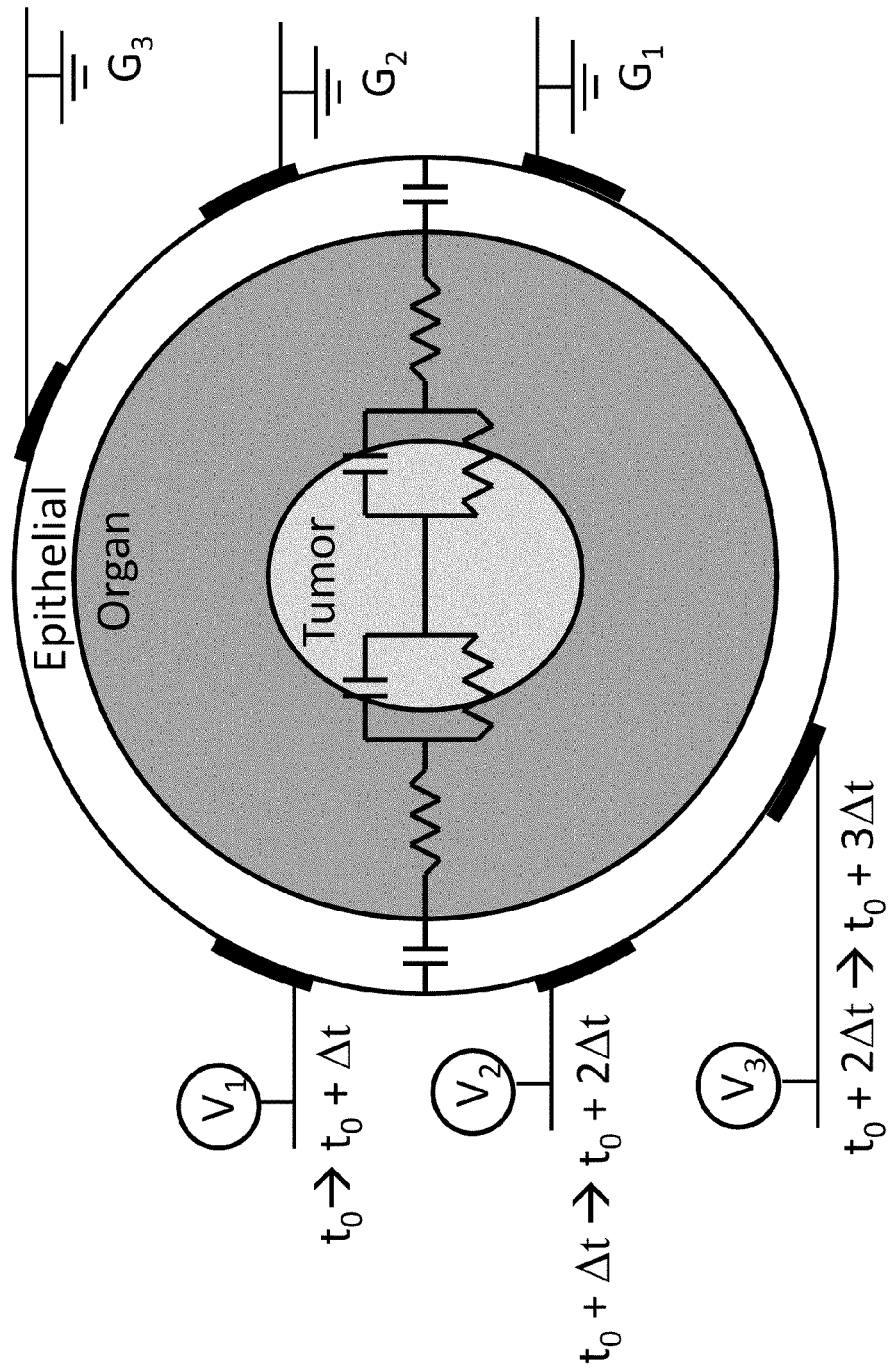
FIG. 2 depicts a noninvasive electrode arrangement for employing integrated pulsed electric field therapy on an aberrant cell mass. In the case shown, the temporal and spatial summation of the ultra-short pulses lead to treatment of the tumor area, and the healthy surrounding cells are left intact. At a given instant, only one pair of energized and grounded electrodes are activated, and after a time delay (k·Δt) an adjacent pair of electrodes become energized.

Epithelial layer is a general tissue type comprised of one or more monolayers of cells in which the cells are connected by tight junctions. Such tissues form linings of organs and other specialized structures. Qualitatively the main barrier of each monolayer consists of two cell membranes. Frog skin and toad bladder are good approximations of endothelial tissue. Due to the ability of ultra-short pulses to electrically "short"

epithelial layers, novel electrode designs can be implemented to generate electric fields within internal organ tumors. Therefore, in another embodiment of methods of the present invention, energized electrodes can be placed around a preselected region (e.g., portion of an organ) of a subject, such as an animal (e.g., human), and the grounded electrode can be inserted into a region of the subject that contains tumor cells. For example, for treating a solid tumor, a ring of energized electrodes can be placed around a portion (e.g., the abdomen) of a patient and the grounded electrode can be inserted into an abdominal tumor to concentrate the electric field, such that only tissue regions surrounding the grounded electrode experience a localized electric field above the threshold for achieving supra-poration. FIG. 1 depicts a representative electrode configuration for treating internal organ tumors with pulsed electric fields, showing energized (gray) and grounded (black) surfaces. In this embodiment, the electrode setup is minimally invasive, as the energized electrodes are non-puncturing, and the grounded electrode can be smaller in diameter than typical needles used in tissue biopsies. However, the grounded electrode can be eliminated by having the electrode opposite the active electrode in relation to the desired treatment area grounded at a given instant in time, resulting in a completely noninvasive pulsed electric field cancer therapy (see FIG. 2). Essentially, the organ is surrounded with an electrode ring/array and a nanosecond pulse is sent through 2 electrodes at a given time. The pulse shorts through the epithelial layer and allows the field to penetrate the tissue. Afterwards another set of electrodes are used, and so on. In this way the field continuously is sufficient (strength and duration) within the tissue to induce electroporation. If only one set of electrodes were used and a microsecond pulse was applied, the field drop would only occur across the epithelial layer.

Similarly, for leukemia, a ring of energized electrodes can be placed around a patient's extremity.

In an embodiment of the method that employs a ring of energized electrodes, the method comprises delivering ultra-short pulses simultaneously around the circumferentially oriented electrodes, such that all plates are energized at a given instant, and generating a single pulse from the temporal summation of the individual pulses capable of inducing supra-poration around the grounded electrode within the organ of interest. While this concept is exemplified herein with regard to supra-poration, its applicability to IRE is also immediately apparent. Furthermore, while a ring-shaped electrode is exemplified, it should be evident that any geometric shape can be used.

Figure 11:
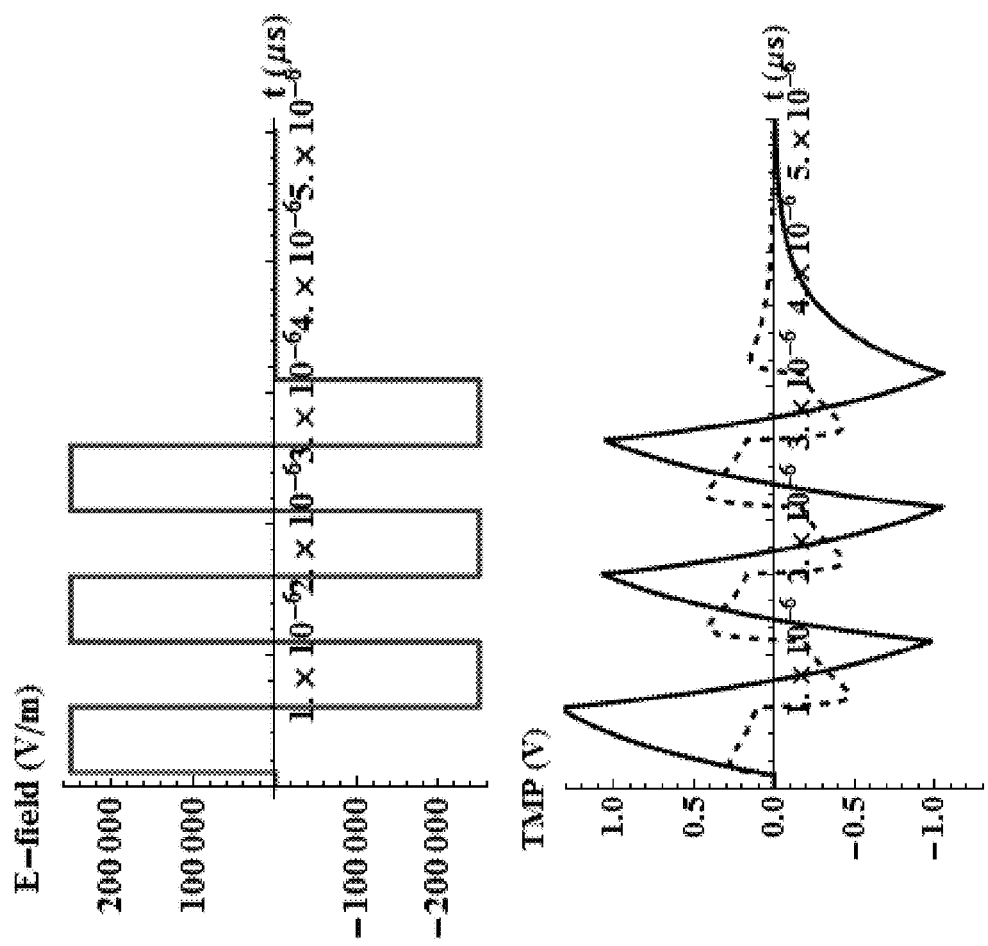
FIG. 11 depicts the results of analytical calculations on transmembrane potential (TMP) for leukemia cells exposed to a bipolar pulse train comprised of ultra-short pulses. The pulse duration has been tuned to equal the charging time of the plasma membrane (~500 ns).

In another embodiment, the electrical pulses are delivered in a series of two nanosecond-range pulses of alternating polarity. Use of alternating polarities reduces or eliminates charge buildup on the electrode. For example, two Nanoknife™ (Angiodynamics, Queensbury, N.Y.) devices can be linked to the same electrode array, and programmed to deliver synched pulses to the electrodes. The first pulse can generate a 2500 V/cm electric field of 500 ns duration. The offset of this pulse is followed immediately by the onset of a second pulse, which generates a −2500 V/cm electric field for 500 ns. Therefore, each pulse can charge the plasma membrane to its critical permeabilizing threshold. Once the TMP approaches its asymptotic value at the fully charged state, the pulse polarity flips and the procedure is repeated. In FIG. 11, the target value of a 1 V TMP on the plasma membrane (solid line) is reached multiple times within the pulse train, while the TMP on the intracellular organelles (dashed line) never charges to the permeabilizing threshold of 1 V. On a tissue level, this allows for the electroporation of regions overlaid by layers of tightly packed cells. A multicellular model emphasizing this embodiment of the invention is given in the Examples below. It is important to note that bipolar pulses are only effective for electroporation if each pulse within the train is long enough in duration to charge the plasma membrane to a permeabilizing level. If this is not the case, the pulses offset each other from fully charging the plasma, and supra-poration effects dominate when the pulse amplitude is increased (see Example 4). Additionally, a delay can be included between pulses within the train, or the total number of pulses within the train can be controlled, to limit the Joule heating in the tissue while still delivering a lethal dose of energy. The repetition rate of pulse trains can also be controlled to minimize interference with, and allow treatment of vital organs that respond to electrical signals, such as the heart.

The concept of alternating polarity of pulses can be extended to the use of multiple electrodes. For example, a combination of three electrodes can be used to deliver three sequential sets of alternating polarity pulses to a target tissue. More specifically, Electrode A can be used to deliver a 500 ns pulse at 1000 V at a starting time (T=0) and a 500 ns pulse at −1000 V at T=1 µs. Electrode B can be used to deliver a 500 ns pulse at 1000 V at T=500 ns, and a 500 ns pulse at −1000 V at T=1.5 µs. Electrode C can be used to deliver a 500 ns pulse at 1000 V at T=1 µs, and a −1000 V pulse at T=2.0 µs. Of course, this concept can be applied using any numbers of electrodes and pulse times to achieve highly directed cell killing.

As mentioned above, the present invention provides a method for treating aberrant cell growth in animals. In general, the method of treating comprises temporarily implanting one or more electrodes, which may be present on the same or different devices, into or immediately adjacent an aberrant cell region, and applying an electrical field to the aberrant cell region in ultra-short multiple pulses or bursts over a prescribed or predetermined period of time to cause irreversible cell death to some or all of the aberrant cells. Preferably, irreversible damage to healthy cells in proximity to the aberrant cells is minimal and does not result in significant or long-lasting damage to healthy tissues or organs (or a significant number of cells of those tissues or organs). According to the method of the invention, cell killing is predominantly, essentially, or completely due to non-thermal effects of the electrical pulsing. The method further comprises removing the electrode(s) after suitable treatment with the electrical fields. As a general matter, because some embodiments of the method involve temporary implantation of relatively small electrodes, it is minimally invasive and does not result in the need for significant post-treatment procedures or care. When the embodiment is such that electrodes are placed externally to the subject, it is completely noninvasive and requires no post-treatment procedure or care. In either case, it does not result in significant ancillary or collateral damage to the subject being treated.

In practicing the method, the number of electrodes, either on a single or multiple devices, used can be selected by the practitioner based on the size and shape of the tissue to be treated and the size and shape of the electrode. Thus, embodiments of the invention include the use of one, two, three, four, five, or more electrodes. Each electrode can be independently sized, shaped, and positioned in or adjacent the tissue to be treated. In addition, the number and spacing of electrodes on a single device can be adjusted as desired. The location, shape, and size of electrodes can be selected to produce three-dimensional killing zones of numerous shapes and sizes, allowing for non-thermal treatment of aberrant cell masses of varying morphologies.

The method of the invention encompasses the use of multiple electrodes and different voltages applied for each electrode to precisely control the three-dimensional shape of the electric field for cell killing. More specifically, it has been found that varying the amount of electrical energy emitted by different electrodes placed in a tissue to be treated allows the practitioner to finely tune the three-dimensional shape of the electrical field that irreversibly disrupts cell membranes, causing cell death. Likewise, the polarity of electrodes can be varied to achieve different three-dimensional electrical fields. Furthermore, one of the advantages of embodiments of the invention is to generate electric field distributions that match complex tumor shapes by manipulating the potentials of multiple electrodes. In these embodiments, multiple electrodes are energized with different potential combinations, as opposed to an "on/off" system like radio frequency ablation, to maximize aberrant tissue treatment and minimize damage to surrounding healthy tissue.

According to the method of the invention, the separation of the electrodes within or about the tissue to be treated can be varied to provide a desired result. For example, the distance between two or more electrodes can be varied to achieve different three-dimensional electrical fields for electroporation or supra-poration. The three-dimensional shape can thus be set to kill diseased cells and tissues, but partially or completely avoid healthy tissue in situations where the interface between healthy and diseased tissue shows a complex three dimensional shape.

The amount of heat generated during treatment of aberrant cells is minimized by the methods of the invention. However, to better ensure that cell killing is a result of non-thermal effect, and to better protect healthy tissue surrounding the site of treatment, the method can further comprise cooling the electrodes during the treatment process. By applying a heat sink, such as a cooling element in an electrode, generation of heat in and around tissue in close proximity to the electrodes can be minimized, resulting in a more consistent application of IRE and supra-poration to the tissue and a more controlled application of cell killing to only those tissues desired to be treated.

The method of the invention, in embodiments, includes the use of electrodes of different sizes and shapes. Studies performed by the inventors have shown that the electrical field distribution may be altered by use of electrodes having different diameters, lengths, and shapes. Thus, the use of different sizes and shapes of conducting surfaces can be used to control the electrical fields used for cell killing. In certain embodiments, the method includes the use of a variable size electrode. For example, an electrode may be used that, in one configuration has a relatively small diameter, which is used for minimally invasive implantation of the electrode into the site to be treated. Once inserted, a sheath or other covering can be retracted to allow expansion of the electrode tip to a different size for application of the electric field. After treatment, the sheath can be moved to cover the tip again, thus reducing the size of the tip to its original size, and the electrode withdrawn from the treated tissue. The expandable element can be thought of as a balloon structure, which can have varying diameters and shapes, depending on original material shape and size.

The methods of the invention comprise, in embodiments, treatment of tissue surrounding a site of aberrant cell growth. In embodiments, this treatment causes cell killing of some healthy cells surrounding the aberrant cell growth. For example, in treating an invasive or aggressive tumor, it is often advisable to eliminate a zone of apparently healthy cells surrounding a tumor site to improve treatment outcome by destroying tumor cells that have invaded the healthy tissue outside of the defined tumor.

In other instances, treatment of tissue surrounding a site of aberrant cell growth includes causing reversible electroporation of cells of the surrounding tissue. The reversible electroporation can be an unavoidable consequence of the method, but can also be an intended result. In either case, reversible electroporation can be a mere side-effect of the treatment, or can be used as a secondary treatment. More specifically, reversible electroporation can be used to cause cells of healthy tissue surrounding an aberrant cell mass to have different physical and biochemical properties than it had prior to treatment. For example, bioactive agents can be introduced into the reversibly electroporated cells. The bioactive agents can be agents that cause the healthy cells to be killed. In such embodiments, additional cell killing, under controlled conditions, can be effected in healthy tissue. Alternatively, the bioactive agents can be agents that protect the cells from destruction, for example by immune cells that respond to the tissue injury resulting from the electroporation treatment of the aberrant cells.

In embodiments, the method for treating aberrant cell growth in animals is a method of treating a subject suffering from a solid tumor or a region comprising aberrant cells. It thus may be a method of treating a subject suffering from cancer. Using different terminology, the method can be a method of treating a tumor region or a method of treating cancer. As such, the method can be a method of treating either a benign tumor or a malignant tumor. In exemplary embodiments, the method is a method of treating a subject suffering from diseases and disorders that affect tissues characterized by relatively high permittivity, such as the outer layer of the pancreas and bone. Therefore, exemplary embodiments of the present invention are methods that treat pancreatic cancer and leukemia.

In clinical settings, the method of treating according to the invention can have ameliorative effects or curative effects. That is, a method of treating a subject can provide a reduction in aberrant cell growth, such as of a tumor region. Likewise, it can provide a reduction in the mass of the aberrant cell growth, such as tumor region size. Further, it can provide total ablation of the aberrant cell mass, such as the entire tumor mass.

The method of the invention can include a single round of treatment or two or more rounds of treatment. That is, the method of treating aberrant cells, either intentionally or as a result of the size or shape of the aberrant cell growth mass, can result in less than complete destruction of the mass. In such a situation, the method can be repeated one or more times to effect the desired level of mass reduction. As the method of the invention is relatively minimally invasive, multiple rounds of treatment are not as harmful to the patient than multiple rounds of traditional surgical intervention.

The method of the invention can be part of a multi-modal treatment. The method thus may comprise other cell-killing techniques known in the art. For example, the method may further comprise exposing a tumor region to radiation, or treating the patient with a chemotherapeutic agent. It likewise may be performed after or between surgical intervention to remove all or part of a tumor region. Those of skill in the art are fully aware of the parameters for treatment with other modalities; thus, details of those treatment regimens need not be detailed herein.

The methods of the invention are performed using one or more electrodes that provide cell-killing electrical pulses to target cells and tissues. Numerous electrodes for electroporation are known in the art and can be used in accordance with the invention. Likewise, numerous devices comprising electrodes for electroporation are known in the art. Those of skill in the art are free to chose appropriate electrodes and devices based on the parameters for a particular application (e.g., tumor size, tumor shape, electrode size, electrode shape).

EXAMPLES

The invention will be further explained by the following Examples, which are intended to be purely exemplary of the invention, and should not be considered as limiting the invention in any way. As a general background to the Examples, it is noted that the inventors and their colleagues have successfully demonstrated that finite element models (FEMs) can accurately predict treatment outcomes of pulsed electric field therapies for tissue ablation.

Example 1

Optimization of Voltage Parameters and Nanorod Concentrations for Selectively Killing Leukemia Cells In Vitro Gold nanorods can be used to enhance the selectivity of pulsed electric field therapies to treat leukemia, a cancer that starts in the bone marrow and causes a large number of blood cells to be produced. Treatment of leukemia depends on the type and extent of the disease but often involves chemotherapy or radiation therapy. In autologous stem cell transplantation, stem cells from the patient's own marrow or blood are obtained and engrafted after the patient receives an intense dose of chemotherapy or radiation in an attempt to restore hematologic and immunologic function following treatment. There is the potential for disease recurrence if the engrafted stem cells contain even a single leukemic cell. Gold nanorods combined with antibody targeting techniques provide a means to selectively kill leukemic cells through the localized amplification of an applied external electric field. This treatment can be used as either an alternative to stem cell transplantation or as a means to purge stem cells of leukemia prior to engraftment.

In this Example, sample preparation is performed using previously established protocols developed by Lapotko et al. (Lasers SurgMed, 2006). Specifically, cryopreserved samples of primary human cells derived from the bone marrow of leukemia patients (acute B-lymphoblast leukemia) and healthy donors are used. Normal bone marrow samples have no tumor cells and leukemic samples are comprised mainly of tumor cells (up to 98%) in samples from different patients. Normal and tumor samples are prepared and analyzed as separate samples in 6 well-plates, but they are treated with the same protocols. The trial groups (Table 1) include a control group without nanorods and antibodies (−NR, −Y), an enhancement group (+NR, −Y), and a targeting group (+NR, +Y). Gold nanorods are purchased (Nanopartz) with a dense coating of hydrophilic polymers for conjugation to secondary antibody and uniform suspension. Leukemia cells express diagnosis specific genes that are determined individually for each patient using standard clinical protocols developed by Jennings and Foon (Blood, 1997). Flow cytometry is used for phenotyping and specific monoclonal antibodies raised against cell membrane receptors corresponding to specific genes are used for each sample of tumor cells. For different patients, different monoclonal antibodies yield different expression levels and an optimal monoclonal antibody is used for each patient-specific sample in all experiments. In the targeting trial group, samples are incubated for 30 minutes with their corresponding primary antibody that selectively attaches to blast cells. In the enhancement and targeting trial group, samples are incubated for an additional 30 minutes with gold nanorods that are conjugated with a secondary antibody that has a high coupling efficiency for primary antibody. Additionally, R-phycoerythrin (PE), a fluorescent dye (#P9787, Ted Pella Inc.) factory conjugated with a tertiary antibody that has a high coupling efficiency for secondary antibody, is used as a marker for nanorods in quantifying distribution. PE is incubated with samples for 30 minutes. All incubation is performed at 4° C. to minimize physiological processes and allow for the efficient antibody-receptor or antibody-antibody interactions.

The sample size for each pulsing protocol with varying nanorods concentrations is 4 (Table 1). Sample size was calculated based on a one-sided t-test with an alpha value of 0.05, a power of 0.80, and an anticipated Cohen's d of 2.00 (considered to be a large effect size). This effect size is consistent with published data on cell survival following IRE as compared to untreated controls. A conservative estimate calculates the value of Cohen's d with a mean percent survival of 90% (0.3 standard deviation) for untreated controls and 30% (0.3 standard deviation) for cells treated with IRE for inducing cell death.

For the electric pulse protocol, the ECM 830 Square Wave Electroporation System (BTX Harvard Apparatus) is used to induce IRE in cell suspensions. The device is capable of generating a wide range of voltages (5 to 3000 V) and pulse durations (10 μs to 10 s). Additionally, the device can be used in combination with a variety of specialty electrodes (BTX Harvard Apparatus). Specifically, cells are electroporated using the BTX Petri Pulser. This device is designed to electroporate cells grown in a 6-well plate and is comprised of 13 gold plated electrodes spaced 2 mm apart. Because there is no commercially available nanosecond pulsed generator for bioelectric studies, one is constructed according to a previously established protocol developed by Sun et al. (Dielectrics and Electrical Insulation, IEEE Transactions on, 2007). The supra-poration generator can be used with the BTX Petri Pulser and provides a 10 ns pulse duration with a rise time of approximately 2 ns and an amplitude up to 35 kV. The experiments are designed around these device restrictions (Table 1). Immediately prior to exposure to electric pulses, samples are imaged to perform a nanorod distribution analysis. After exposure to electric pulses, the samples are incubated for 12 hrs prior to performing a subsequent nanorod distribution analysis and cell viability analysis to allow adequate time for the induction of cell death following supra-poration.

A CCD camera (U2C-145415, Ormins Ltd.) is used with a fluorescent light microscope (Leica DMI6000B, Leica Microsystems) in order to image and quantify the distribution of nanorods around individual cells and the cell viability following supra-poration. Bright field images of cells are taken of all samples and overlaid with fluorescent images in all trial groups. Leica image processing software is used to reconstruct a representative image of each entire well by automatically tiling individual field of view images. The bright field images are used to distinguish cell type and dimension, and the fluorescent images are used to quantify nanorod association with the cell membrane and cell death. To quantify nanorod association with the cell membrane, a standard "green" fluorescent excitation mode is applied, and intensity measurements are recorded both at the cell membrane and throughout the rest of the sample using the Leica image processing software. The peak image amplitude is treated as an estimation of the total number of nanorods. The CCD camera is calibrated using several different known concentrations of homogeneous dispersions of nanorods in water. Previous studies have shown that the mean pixel amplitude of a fluorescent signal is almost linearly proportional to the concentration of nanorods. To analyze cell viability, all samples are stained with propidium iodide (PI), and a standard "red" fluorescent excitation mode is applied. PI gets taken up in cells with compromised plasma membranes, such that cells that are counted as PI-positive are considered dead, and cells that are counted as PI-negative are considered live. A software program in LabVIEW can be used to analyze the reconstructed well images and distinguish dead from live cells to output a viability percentage. Additionally, the software can determine the concentration of nanoparticles around each cell.

A Multi-way ANOVA with SPSS software is used to determine statistical significance among endpoint measurements for all pulsing protocols, and a TukeyKramer test identifies significant differences between cell response to supra-poration alone or in combination with gold nanorods. Data is presented as mean±standard deviation of 4 independent determinations, and a statistical probability of $P<0.05$ is considered significant. In the tested pulsing protocols (Table 2), electric fields resulting in greater than 90% cell death are considered the threshold for inducing supra-poration with and without the inclusion of gold nanorods.

SOL Multiphysics (version 3.5 a), was selected because of its variety of features and functionality, as well as its capability to integrate seamlessly with MATLAB (Chiu and Stuchly, Biomedical Engineering, IEEE Transactions on, 2005). For the model, the "quasi-static, electric" mode of COMSOL was selected for its ability to perform a time-harmonic analysis of conducting and dielectric materials with small currents in the (r,z)-plane and a negligible coupling between the electric and magnetic fields. This mode essentially solves the complex Laplace equation:

$$-\nabla \cdot (\sigma \nabla V) - \varepsilon_o \varepsilon_r \nabla \cdot \left(\frac{\partial \nabla V}{\partial t}\right) = 0$$

This equation accounts for the resistive and capacitive components of bone, which must be included when modeling heterogeneous tissue. The offset of a square wave pulse causes the capacitive current to change direction within biological tissue, and the duration of the pulse determines the frequency at which the current changes direction. Therefore, the pulse duration can be correlated to data defining the conductivity and relative permittivity of bone and bone marrow at various frequencies. Furthermore, the frequency dependence of the pulses on the electric field distribution within the tissue can be evaluated in order to distinguish electroporation from supra-poration protocols.

TABLE 2

Trial groups, pulsing parameters, and nanorod characteristics for in vitro experiments.

| Trial Group | Applied Voltage (N = 4) | Pulse Duration | Cell Line | Conc. | Number of Pulses | Frequency |
|---|---|---|---|---|---|---|
| Control (−NR, −Y) | 0, 50, 100, 150, 200, 250, and 300 Volts | 10 μs | Normal Cancer | — | 100 | 1 Hz |
| | | | Normal Cancer | | | |
| Enhancement (+NR, −Y) | 0, 50, 100, 150, 200, 250, and 300 Volts | 10 μs | Normal Cancer | 0.1, 0.5, and 1 mg/ml | 100 | 1 Hz |
| | 0, 5, 10, 15, 20, 25, and 30 kV | 10 ηs | Normal Cancer | | | |
| Targeting (+NR, +Y) | 0, 50, 100, 150, 200, 250, and 300 Volts | 10 μs | Normal Cancer | 0.1, 0.5, and 1 mg/ml | 100 | 1 Hz |
| | | 10 ηs | Normal Cancer | | | |

Example 2

Computational Model for Investigating the Electric Field Distribution Within Bony Tissues Imaging can be combined with computational modeling to provide insight into the unintuitive, highly complex interaction of electric fields with biological tissue. The electric field distribution within spongy bone can be determined to quantify treatment areas following supra-poration. Results from in vitro experimental data can be used to define electric field thresholds for killing bone marrow cells in the model. Further, image reconstructions and treatment area calculations obtained from in vivo experiments further refine the model geometry and properties.

A mathematical simulation for predicting the electric field distribution within a spongy bone structure where bone marrow resides among the trabeculae has been developed. A commercial finite element method (FEM) package, COM- The geometry of the FEM was defined as two-dimensional with axial symmetry to simplify computation time. A bipolar electrode, similar to one currently employed in IRE protocols for tumor ablation (AngioDynamics Inc.), was inserted into a spongy bone structure filled with bone marrow. The bipolar electrode was 4 mm in diameter, and the exposed energized and grounded portions of the electrode were selected to be 6 mm in length. The diameter of the randomly distributed bone marrow regions were selected to be 1 mm, as estimated by scanning electron micrographs of spongy bone. The overall geometry was large enough (4 cm×4 cm) to avoid outer surface boundary effects. Dirichlet and Neumann boundary conditions are incorporated into COMSOL and can be employed by specifying the boundary conditions to each interface accordingly. The boundaries of the energized and grounded electrodes were taken to be 1 kV and 0 V, respectively. 1 kV falls within the range of voltages commonly employed in IRE and supra-poration procedures and is used initially as a reference to gain insight into both procedures. The boundaries between the spongy bone and bone marrow were treated as continuous, while all remaining boundaries were treated as electrical insulation. Although bone marrow is in fact a composition of various tissues including adipose tissue, reticular tissue, lymphoid tissue, hematopoietic tissue, and blood, it was treated as a homogeneous material in the computation.

By employing pulses with a high frequency or durations shorter than the charging time of the plasma membrane, the electric field distribution within heterogeneous tissue resembles that of homogeneous tissue. Ultra-short (nanosecond) pulses can be used to penetrate tissue heterogeneities with a relatively high permittivity, whereas microsecond pulses are not as efficient. It is evident that the nanosecond pulse is better suited to induce supra-poration in bone marrow as a potential treatment for leukemia.

Subdomain integration was performed to calculate the treated area inside bone marrow regions for a variety of electric field thresholds. For example, if the electric field threshold to induce cell death in bone marrow following supra-poration is determined to be 1000 V/cm, 0.1 $cm^2$ of bone marrow is treated. However, if through the incorporation of gold nanorods this electric field threshold drops to 500 V/cm, 0.3 $cm^2$ of bone marrow is treated. Interestingly, the microsecond pulse is better suited to treat a large amount of bone without affecting the bone marrow. This shows the potential of supra-poration to treat other types of bone cancer.

In order to develop the model described above so that it can be incorporated with x-ray micro-CT scan data, the geometry of the FEM needs to be redefined as 3D. Then, the iso-surface feature of MATLAB can be used to convert the in vivo 3D image reconstructions into a format that can be imported into COMSOL to create a custom FEM geometry for each patient. The model can be extended to include the Pennes Bioheat equation for predicting temperature distributions. This will allow surgeons to ensure that the pulsing parameters do not create a temperature rise in the tissue that causes thermal damage so that the non-thermal benefits of IRE and supra-poration are maintained. Furthermore, the dielectric properties of the tissue can be altered in the simulation until the predicted treatment area, based on the electric field thresholds, matches the treatment area calculated histologically for the corresponding section of tissue. Animals can be tested and an average conductivity and relative permittivity for each pulse duration can be calculated. The goal is to lower the applied voltage such that only leukemic cells with bound gold nanorods in bone marrow regions will be killed.

Example 3

Cell Death in Bony Tissue Using Pulsed Electric Fields

To demonstrate that pulsed electric fields can safely and predictably induce cell death in bony tissue, a rabbit model is used as the animal of study because techniques have been established for performing imaging and histological analysis on bony substructures in rabbits. Like humans, rabbits have a well developed haversian system, making them ideal candidates for obtaining translatable results from experiments on bone substructures. Six-month old rabbits are used because it is known that they achieve skeletal maturity at nineteen to twenty-four weeks. The IRE and supra-poration pulse generators are used in conjunction with a custom made bipolar electrode (4 mm in diameter) to deliver the electric pulses.

Two IRE pulsing protocols and two supra-poration pulsing protocols are implemented for a comparison of treatment areas (Table 2). For each of the trial groups, including an untreated control group, four rabbits are utilized, thereby requiring a total of 20 rabbits. Rabbit numbers were calculated based on a one-sided t-test with an alpha value of 0.05, a power of 0.80, and an anticipated Cohen's d of 2.00 (considered to be a large effect size). Using four rabbits for treatment area calculations account for variations in bone structure and tissue response.

Prior to surgery, rabbit femurs are imaged using micro-CT scanning Rabbits are sedated under isoflurane anesthesia using a mask. The left hind-leg is extended and held in place with a strap. The distal femoral is chosen as the region of interest, because it has a sufficient, continuous spongy bone structure. A commercially available low dose in vivo x-ray micro-CT scanner is utilized (Skyscan 1076, Micro Photonics Inc.). The device is capable of performing non-invasive slice imaging and 3D image reconstruction from small animals, such as rabbits. The technique can capture a cross-section up to 17 mm in length along any region of the specimen, and the images have pixel sizes as fine as 9 pm. The data is used to create realistic 3D images and to calculate internal morphological parameters. The 3D images are imported into COMSOL to create a customized FEM geometry for each rabbit. In vivo micro-CT scanning of rabbit distal femurs is repeatable and reproducible and can be used with confidence to measure differences in trabecular bone architecture. Five in vivo scans of the left hind-leg of each rabbit are performed within approximately 30 minutes, with x-ray exposure lasting under 10 minutes.

TABLE 3

Trial groups and pulsing parameters for in vivo experiments

| Trial Group (N = 4) | Voltage | Pulse Duration | Number of Pulses | Frequency |
| --- | --- | --- | --- | --- |
| Control | — | — | — | — |
| IRE 1 | 250 V | 10 µs | 100 | 1 Hz |
| IRE2 | 500 V | 10 µs | 100 | 1 Hz |
| Supra-poration 1 | 10 kV | 10 ns | 100 | 1 Hz |
| Supra-poration 2 | 30 kV | 10 ns | 100 | 1 Hz |

Following imaging, rabbits are maintained under anesthesia, and the bipolar electrode is advanced centrally into the distal femur of the restricted left hind-leg until the energized and grounded surfaces are within the tissue. The x-ray micro-CT scanner is used to ensure proper placement of the electrode. Following delivery of the pulsing protocols, the electrode is removed, and the wound is closed in a routine fashion. Gold nanorods act as dense x-ray absorbing agents, further justifying the use of x-ray micro-CT in this experiment. Rabbits are humanely euthanized 12 hrs post-treatment, to allow adequate time for the induction of cell death following IRE and supra-poration.

After sacrifice, all left femurs are harvested and reserved for histological analysis. Histology specimens are stripped of surrounding soft tissues, fixed in 10% neutral formalin, and embedded in paraffin. Square fragments of tissue are enumerated in a grid format to ensure the spatial location of each tissue fragment is known and can be correlated to regions of injury. Thick sections of 5 µm are taken longitudinally around the electrode implantation site using a microtome (Microm International). The sections are stained with hematoxylin and eosin and imaged on an inverted microscope (Leica DMI6000B, Leica Microsystems). Treatment area is determined through an examination of four sections from each specimen for regions of necrosis. There is a sharp delineation between normal and necrotic tissue following the in vivo application of pulsed electric fields. Images are imported into LabVIEW, and a software program can be used to trace the delineation lines and calculate the internal areas within regions of bone marrow. The measurements are imported into COMSOL to refine the properties of the computational model to better predict treatment outcomes.

A Multi-way ANOVA with SPSS software is used to determine statistical significance among endpoint measurements for all pulsing protocols and a Tukey-Kramer test identifies significant differences in treatment area measurements between IRE and supra-poration. Data is presented as mean±standard deviation of four independent determinations, and a statistical probability of $P<0.05$ is considered significant.

This novel nanoparticle-mediated pulsed electric field therapy can be used to purge stem cells of lekumeic cells prior to engraftment in autologous stem cell transplantations, effectively eliminating disease recurrence. This novel therapy can replace autologous stem cell transplantations completely, and patients will no longer be subject to a high risk of infection and toxicity following chemotherapy and radiation. Additionally, this is the first treatment planning model to incorporate nanorods with pulsed electric field therapies. Such a treatment planning model allows surgeons to optimize the electrode geometry, voltage parameters, and nanorod concentrations for varying types of tissue and heterogeneities to ensure that only leukemic cells with bound nanorods receive a lethal dose of IRE or supra-poration.

Example 4

Figure 5:
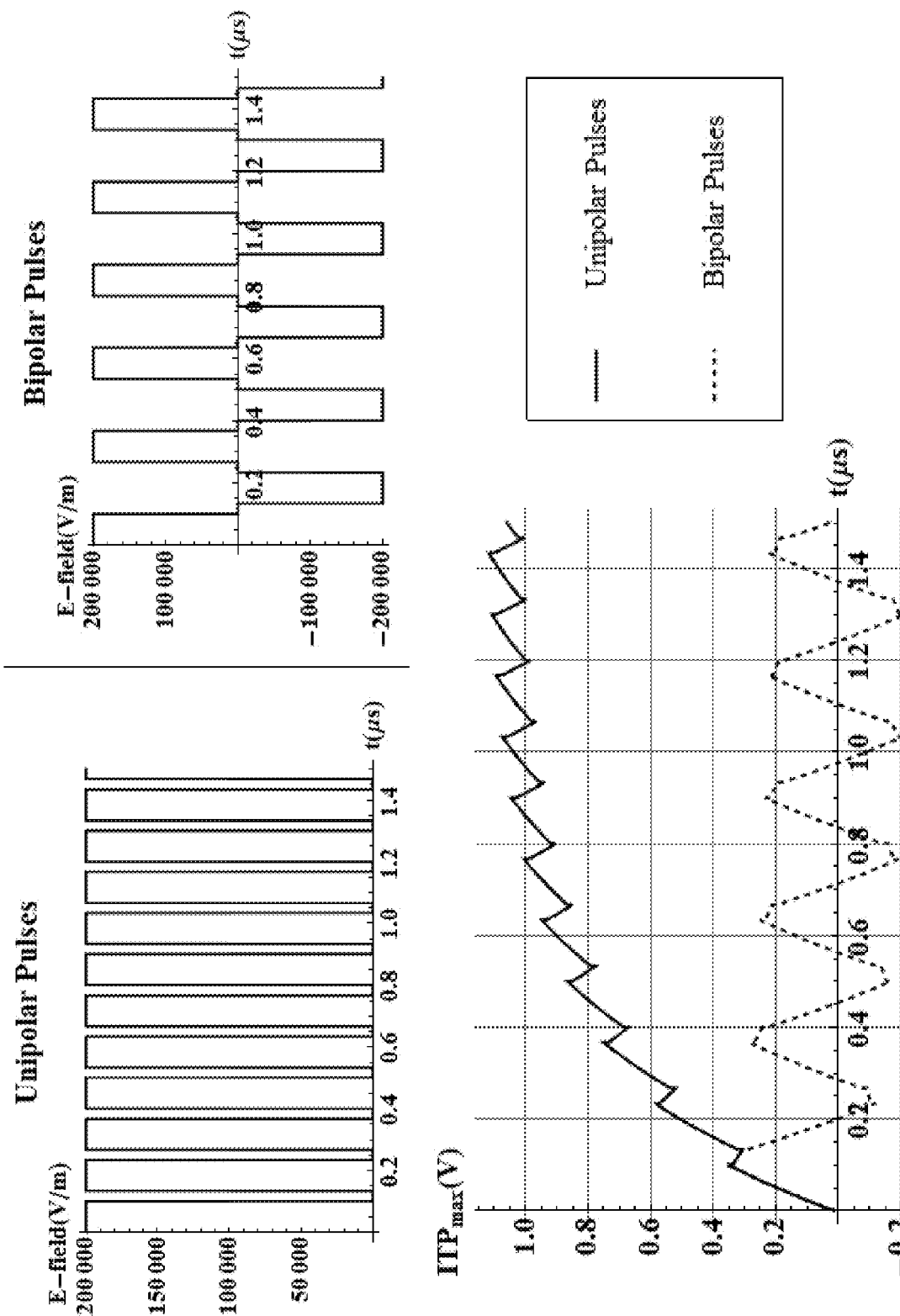
FIG. 5 depicts the results of analytical calculations on transmembrane potential (TMP) for leukemia cells exposed to monopolar and bipolar pulse trains comprised of ultra-short pulses. In each case, the pulse duration (~100 ns) is less than the charging time of the plasma membrane.

Ultra-Short Pulses can be Integrated Temporally and Spatially to Induce Membrane Permeabilization FIG. 5 illustrates the ability for multiple ultra-short pulses to generate an electric field capable of inducing a transmembrane potential large enough to promote irreversible membrane breakdown. When cells are placed in a uniform electric field, and their membranes are treated as spherical, ideal dielectric shells containing and surrounded by a conductive medium, the analytical solution for induced TMP across the plasma membrane and nuclear envelope can be described as a function of time by solving the Laplace equation. The exact formula has been described in the section on detailed description of various embodiments of the invention. The pulse duration was defined to be 100 ns using a Heaviside step function (ideal rise time) in order to investigate the timescale of complete plasma membrane and nuclear envelope charging and discharging, respectively. The duty cycle was defined as 75% (~33 ns delay between pulses), and the pulse amplitude was defined to be 2000 V/cm delivered either uni-directionally (monopolar pulses) or bi-directionally (bipolar pulses). The solution was obtained by frequency domain analysis in Mathematica 7 (Wolfram Research, Inc.) and converted back into the time domain by taking the inverse Laplace transform according to, TMP $(t)=L^{-1}[(TMP(s)]$. Results of the model confirm the hypothesis that if multiple, ultra-short pulses are delivered at a sufficient duty cycle, which temporally and spatially sum to the charging time of the plasma membrane, then cells can remain polarized long enough for the transmembrane potential to reach levels necessary for electroporation. However, when the pulses spatially offset, as is the cases when bipolar pulses are employed, then the TMP never reaches a permeabilizing threshold.

These results can be extended by using finite-element techniques to investigate the limits of pulse directionality. A three-dimensional geometry representative of a multiple-cells enclosed by an epithelial layer was simulated using COMSOL. The "quasi-static, electric" module was selected for its ability to perform a transient analysis of conducting and dielectric materials with small currents in the (r,z)-plane and a negligible coupling between the electric and magnetic fields. The model essentially solves the complex Laplace equation in order to predict the electric field distribution in a non-uniform electric field. The equation accounts for the resistive and capacitive components of tissue, which must be included when modeling heterogeneous systems.

Four application modes were defined to represent the tissue exterior, extracellular space, cytoplasm, and nucleoplasm subdomains. The volume representing the tissue exterior (between the epithelial layer and the electrodes) was filled with a conductive gel ($\sigma=4S/m$, $\in_r=80$), which is commonly used in electroporation procedures to homogenize the electric field. The epithelial layer, plasma membrane, and nuclear envelope forming the interface between the different subdomains were treated as thin sheets of resistive material following the distributed impedance boundary condition:

$$\vec{n}\cdot\vec{J} = \frac{\sigma_m(V_i-V_o)}{d} + \frac{\varepsilon_o\varepsilon_m}{d}\frac{\partial(V_i-V_o)}{\partial t},$$

where J is the total current density (normal) in the membrane, $\sigma_e$, is the conductivity of the membrane, $\in_o$ is the permittivity of a vacuum, $\in_m$ is the relative permittivity of the membrane, d is the thickness of the membrane, and $V_i$ and $V_o$ are the electric potentials inside and outside the membrane, respectively. Lipid bilayers are three orders of magnitude thinner than the dimensions of a typical cell, and the reduction of epithelial cells to a single boundary avoids the creation of extremely fine mesh elements within tight junctions between cells. A perfectly tight epithelium is assumed, in which tight junctions have an infinite resistance.

The thickness of the epithelium (Table 3) was chosen to be four times as thick as the plasma membrane in order to depict a double layer of mesothelial cells encapsulating the tissue section. The surface of peritoneal tissue generally consists of mesothelial cells, but the number of cell layers varies depending on location. To compensate for the fact that the thickness of the epithelium was four times as thick as the plasma membrane, the conductivity of the boundary layer was scaled according to the relation a'=(d'/d)×σ. The remaining horizontal faces of the simulation domain were modeled as electrically insulating, and the vertical faces, representing non-puncturing plate electrodes, were modeled as either electrically insulating, constant potential, or grounded, depending on the electrode activation pattern. Individual, or trains of square-wave electric pulses (0.1 ns rise time) were delivered from the energized electrodes using the function flc2hs, which constructs a smoothed Heaviside step function with continuous second derivative between two different potentials.

The potential distribution within each subdomain was obtained by transiently solving the complex Laplace equation for 13001 degrees of freedom with no external current density in each application mode. The geometry and dielectric properties associated with the cellular subdomains and boundaries are given in Table 1. Calculations of the TMP across the plasma membrane and nuclear envelope were performed by taking the difference between potentials on both sides of the respective membranes. In the first set of experiments, the epithelial layer was treated as a continuous boundary instead of distributed impedance in order to compare our prediction of TMP with analytical techniques of a single cell placed in a uniform electric field. Results are in agreement with those of Pucihar et al. (Annals of Biomedical Engineering, 2006; IEEE Transactions on Biomedical Engineering, 2009), and validate the use of the FEM to investigate multi-cellular system enclosed by an epithelial layer.

Figure 12:
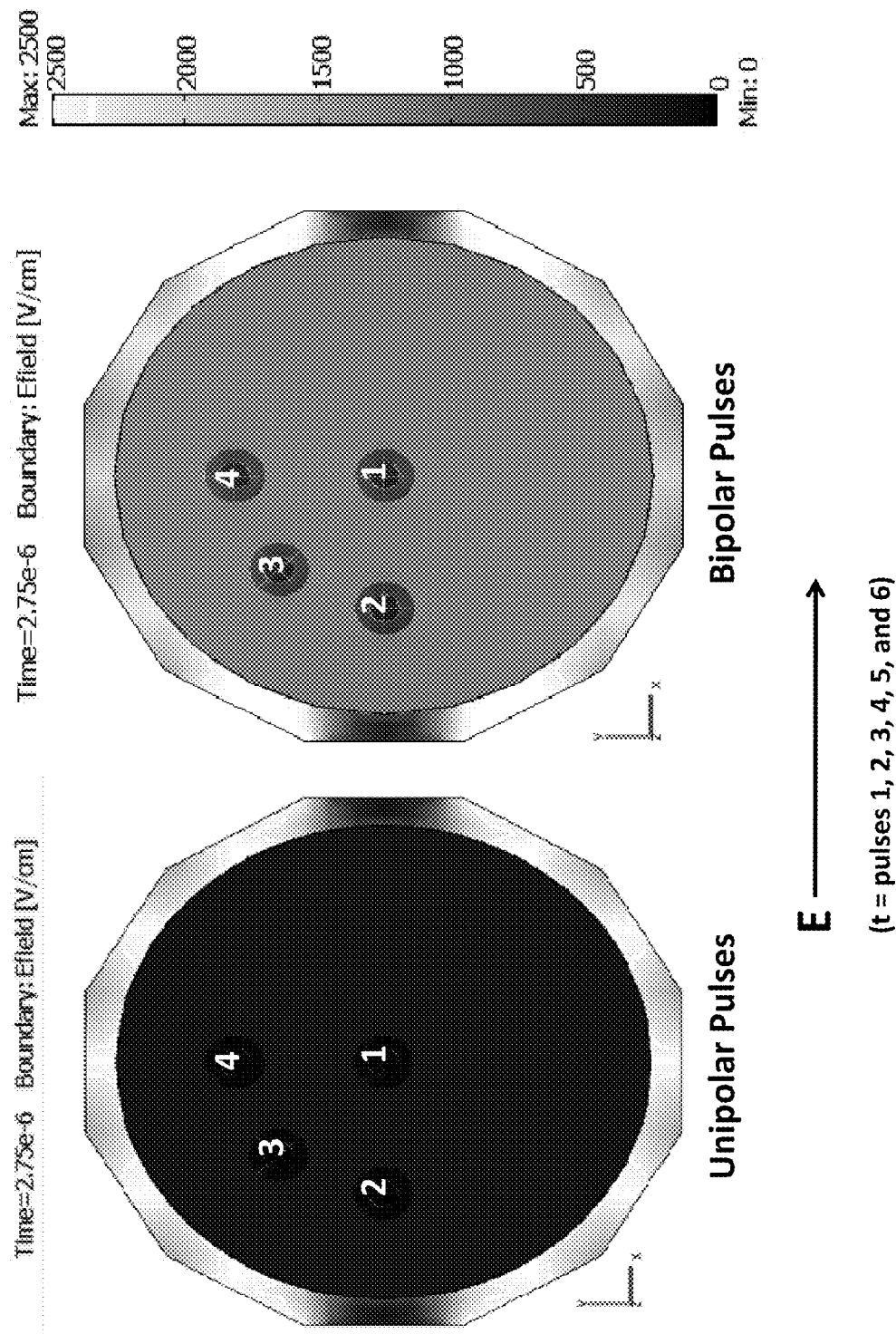
FIG. 12 shows the electric field distribution resulting from the FEM for predicting TMP on a group of cells encapsulated by an epithelial layer. A train of unipolar (left) and bipolar (right) pulses are delivered, and the electric field distribution is shown at the middle of the last pulse in the train. The numbers correspond to locations of cells where plasma membrane TMP was recorded.
Figure 13:
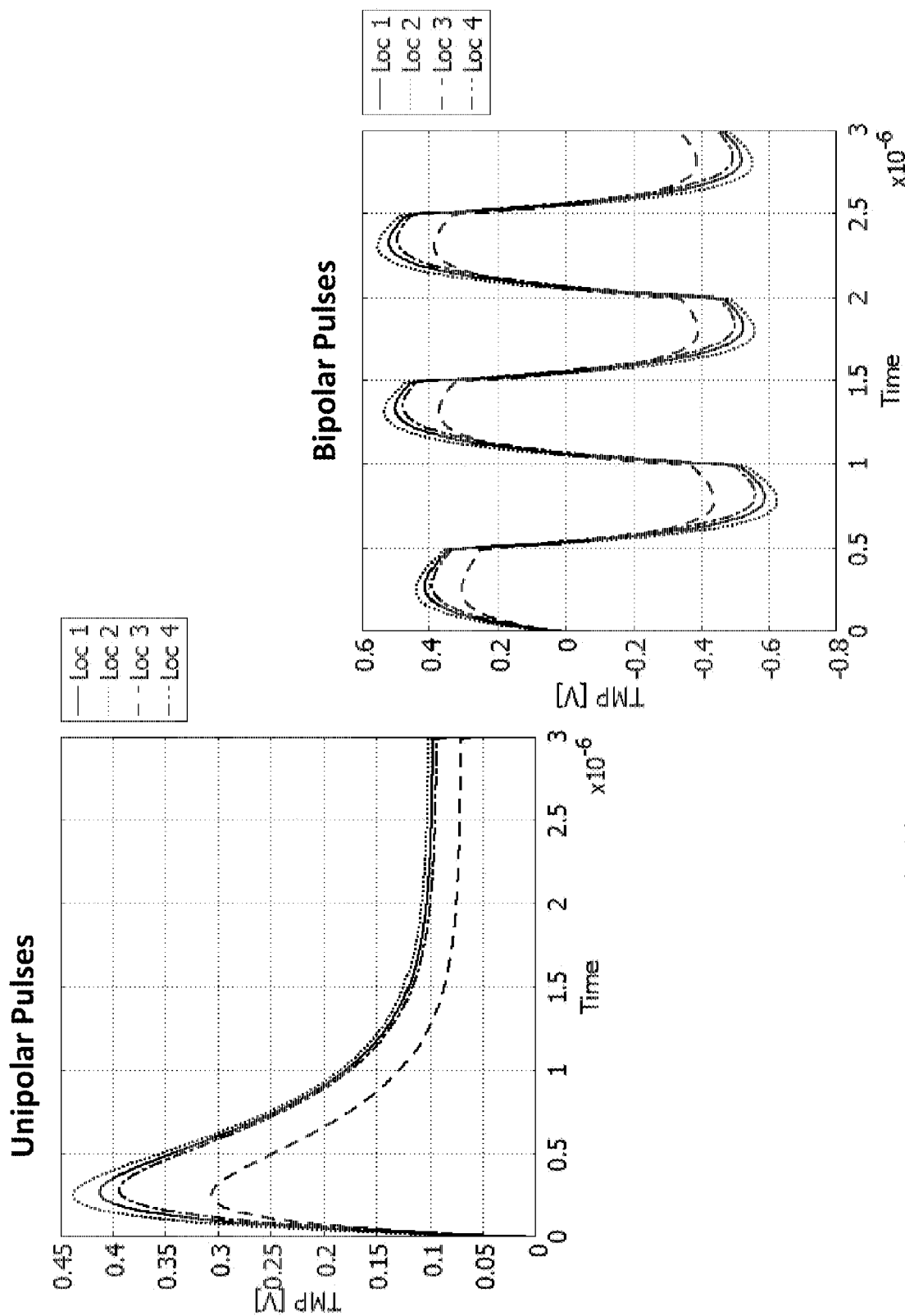
FIG. 13 shows the maximum induced plasma membrane TMP at four different cellular locations in the corresponding FEM model. A train of unipolar (left) and bipolar (right) pulses are delivered, and the maximum TMP is shown throughout the entire pulse in the train.

The potential of the present invention to treat tissues enclosed by epithelial layers is emphasized by the results of the FEM shown in FIG. 12 and FIG. 13. A train of unipolar pulses is compared to a train of bipolar pulses, where both are delivered horizontally across the simulation domain. The pulse duration (500 ns), number (6), amplitude (2500 V/cm), and duty cycle (100%) are held constant in each iteration, such that the polarity is the only parameter of interest. The effects of using unipolar pulses are similar to conventional IRE treatment, in that the integration of pulses results in a single pulse on the order of microseconds. In this case, once the epithelial layer is fully charged, the remaining pulses in the train are not effective for treating the underlying cells. This is evident in FIG. 12, which shows that the epithelial layer shields the electric field from the underlying cells, and in FIG. 13, which shows that the induced TMP on the plasma membrane of the underlying cells drops off after the epithelial layer is fully charged. In the bipolar case, each pulse within the train is tuned to charge the epithelial layer to its critical permeabilizing threshold, and once the TMP approaches its asymptotic value at the fully charged state, the pulse polarity flips and the procedure is repeated. These results, extend those of the analytical model shown in FIG. 11, and indicate that the bipolar pulses are more effective at continually penetrating the epithelial layer and treating the entire tissue volume throughout the duration of the pulse train. In embodiments, each pulse parameter can be increased or decreased according to how long the plasma membrane of the cells comprising a given tissue must be held at a TMP 1 V to induce cell death.

Figure 14:
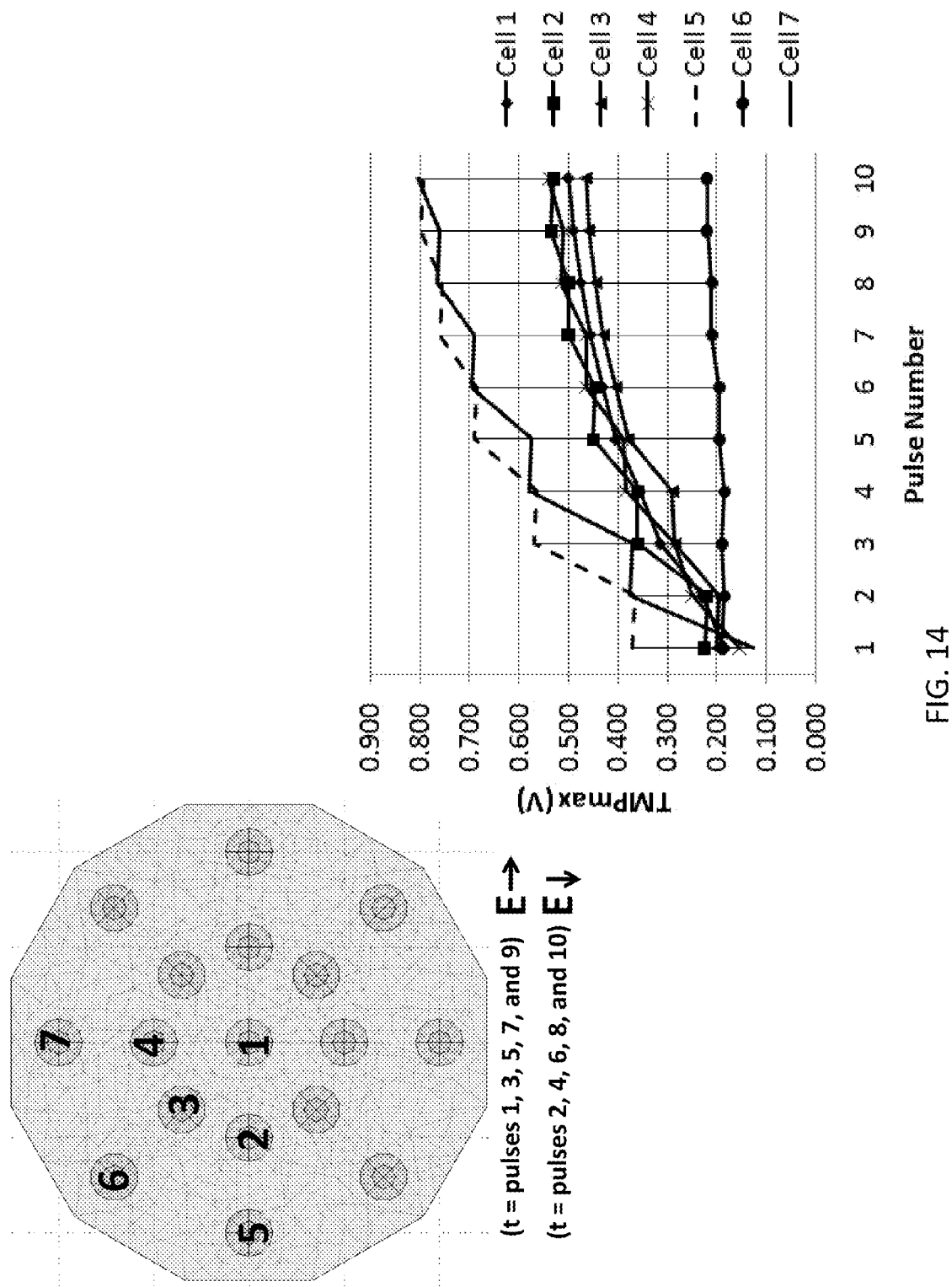
FIG. 14 shows the effect of pulse directionality on induced plasma membrane TMP (right) for a multi-cellular mesh (left). A train of unipolar pulses is implemented, where each sequential pulse within the train is either delivered horizontally (pulses 1, 3, 5, 7, and 9) or vertically (pulses 2, 4, 6, 8, and 10) across the simulation domain. TMP is recorded at seven different cell locations.
Figure 15:
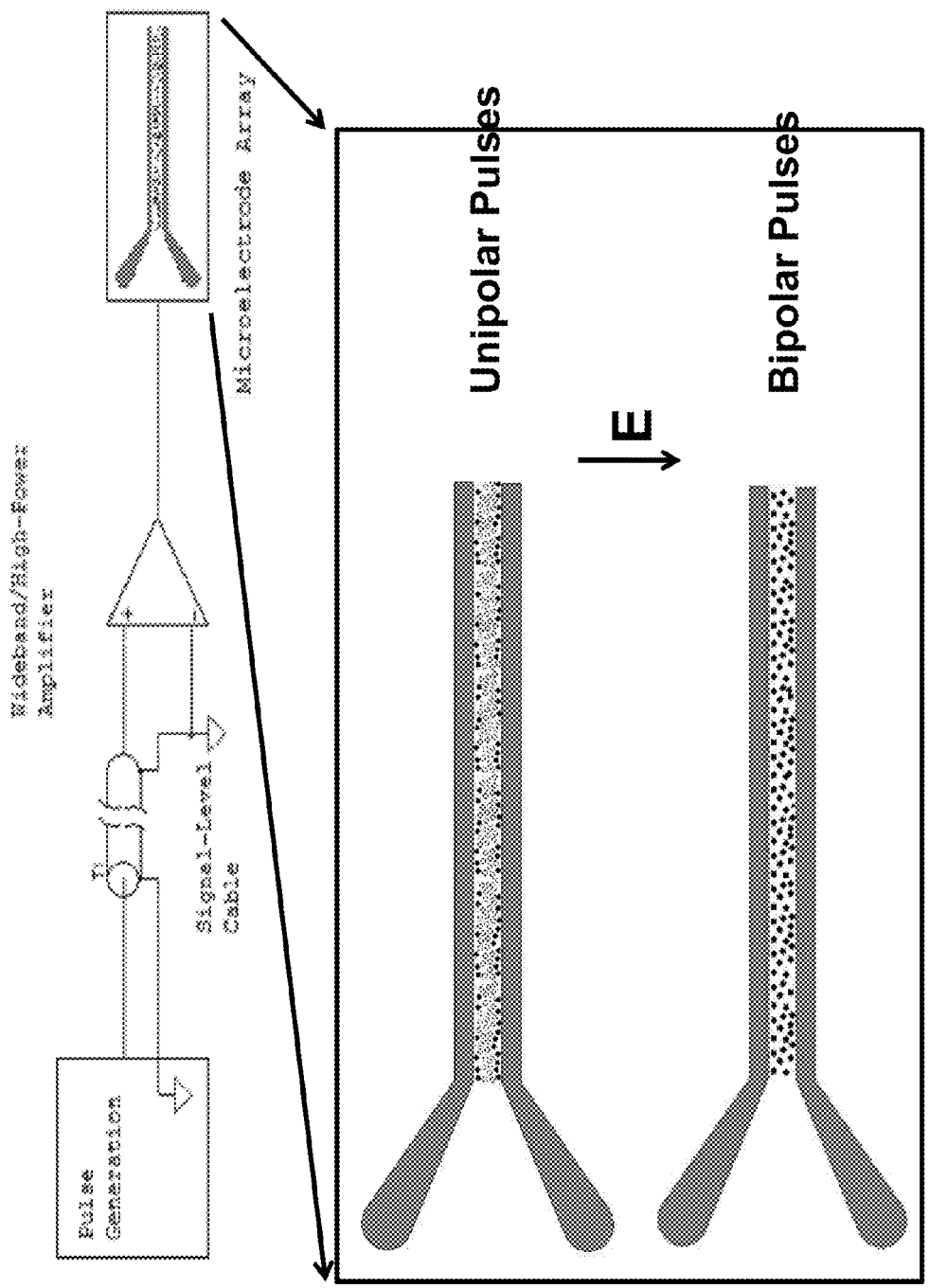
FIG. 15 illustrates a system for varying the region of treated cells in vitro, and two microelectrode arrays with cells cultured in between the electrodes (cut-out). By varying pulse parameters, the region of cell death (shown in black) will be changed.

The potential of the present invention to perform non-invasive, targeted electroporation is emphasized by the results of the FEM shown in FIG. 14. In this simulation, the epithelial layer was removed and only three application modes were defined to represent the extracellular space, cytoplasm, and nucleoplasm subdomains. The potential distribution within each subdomain was obtained by transiently solving the complex Laplace equation for 33397 degrees of freedom with no external current density in each application mode. A train of unipolar pulses is delivered horizontally and vertically across the simulation domain in an alternating fashion. The pulse duration (100 ns), number (10), amplitude (1500 V/cm), and duty cycle (100%) are held constant in each iteration, such that the varying components of the electric field are the only parameters of interest. The maximum TMP is recorded at seven cell locations to investigate the effects of pulse directionality on inducing electroporation. The results shown in FIG. 14 indicate that cells 5 and 7 can undergo IRE while cells 1-4 experience reversible electroporation. Interestingly, cell 6 is spared from all pulsed electric field therapy. Further, if a second train of pulses is delivered at a 45 degree offset from the current train, cells 5 and 7 will be spared. The effect of this embodiment of the invention allows cells 1-4 to experience a permeabilizing field longer than cells 5-7, resulting in a targeted form of electroporation.

Example 5

Figure 6:
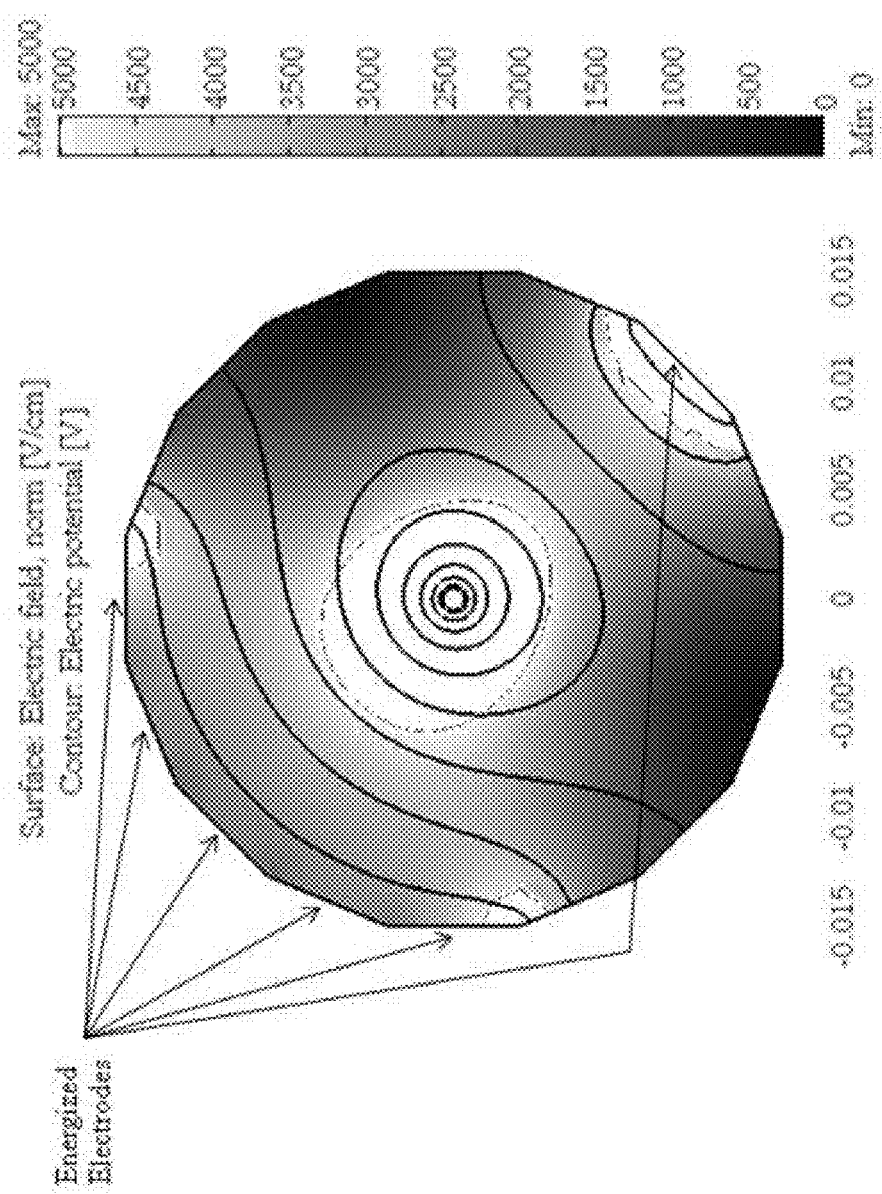
FIG. 6 depicts a model of a custom shaped treatment area undergoing supra-poration according to an embodiment of the invention.

Novel Device Designs Allow for Treatment Area Morphology Control through Electrode Activation Patterns FIG. 6 illustrates the ability of novel electrode designs to control the shape of the treatment area through the combination of ultra-short pulses. Sixteen electrodes are placed non-invasively around a two-dimensional region of tissue, and a ground electrode is inserted into the center of the same region of tissue.

Using similar techniques as described in Example 4, the electric field distribution is predicted when 10 kV, 10 ns square-wave pulses are delivered simultaneously from the energized electrodes with the others set as electrical insulation. The complex Laplace's equation was solved for 2704 degrees of freedom. 10 kV, 10 ns square-wave pulses are delivered simultaneously from the energized electrodes with the others set as electrical insulation. As shown in the figure, a custom shaped treatment area (region enclosed by broken line) of tissue region undergoes supra-poration. Due to the custom electrode activation pattern, the results indicate that a greater amount of tissue is treated on the side of the ground electrode that is closer to the larger number of energized electrodes. The resultant "egg-shape" is just one example, and other electrode activation patterns could be implemented to yield more complex geometries.

Example 6

Ultra-Short Pulses Allow for Heterogeneity Penetration and Treatment Area Location Control In order to calculate the capacitances (C) and resistances (R) in the circuit model of the pancreas, data on the specific conductivity ($\sigma$) and relative permittivity ($\in_r$) of connective tissue (ct) and pancreatic (p) tissue is needed. Biological tissue is neither a perfect dielectric nor a perfect conductor, and the values for $\sigma$ and $\in_r$ are dependent upon the frequency of the applied electric field. In electroporation and supra-poration protocols, voltage is delivered to the electrodes in a square pulse waveform, where most of the energy resides at 0 Hz. Therefore, data for connective tissue (estimated to be similar to wet skin) and pancreatic tissue conductivity and permittivity at 0 Hz is used. After applying input voltage of 10 kV as a square pulse waveform for a specified duration, the voltage drop across the connective tissue can be decreased by reducing the pulse duration into the nanosecond time range.

Figure 7B:
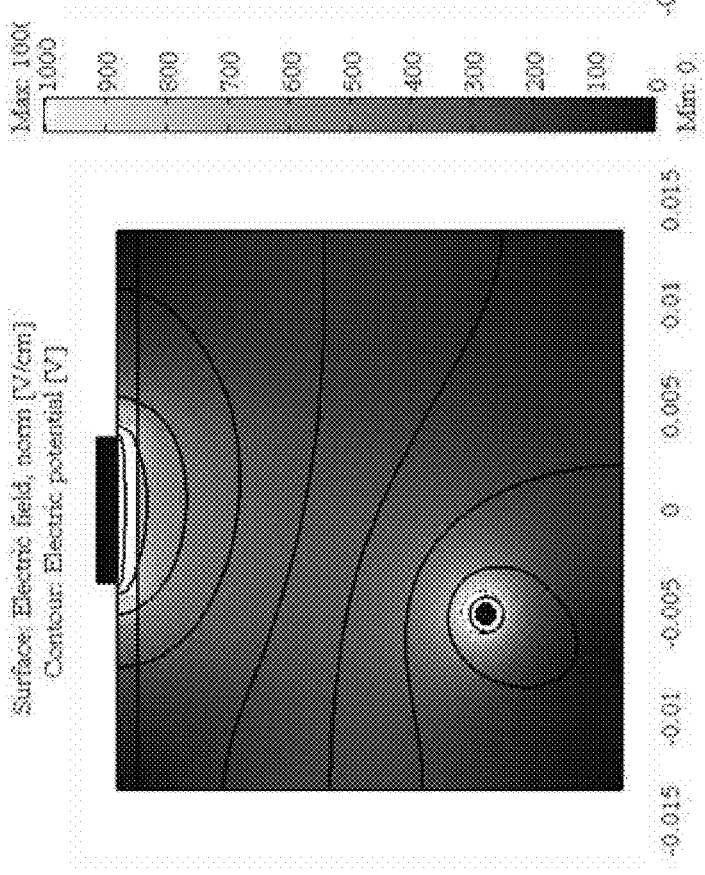
FIG. 7 depicts a model of the treatment area in a pancreas undergoing IRE around an internal ground electrode when the energized electrodes are placed externally around the connective tissue capsule covering the pancreas. Panel A shows treatment with 1000 V and 10 μs square-wave pulses. Panel B shows treatment with 1000 V and 10 ns square-wave pulses.
Figure 7A:
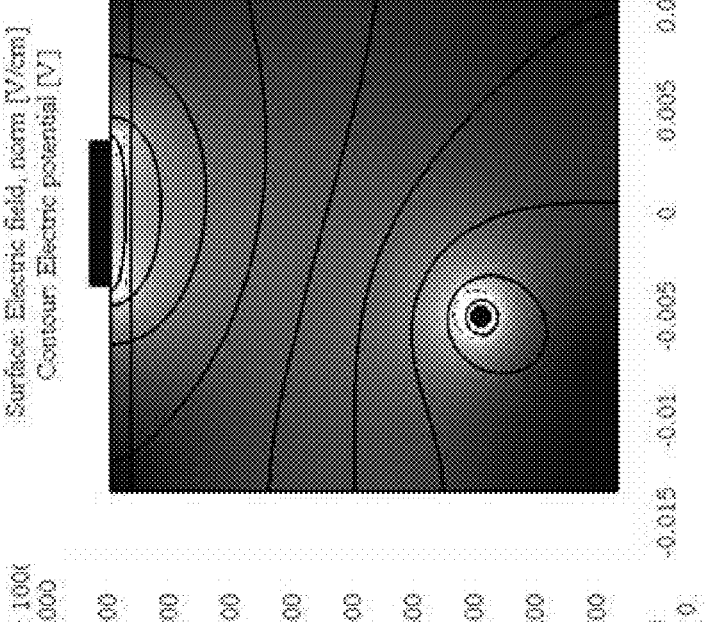

FIG. 7, Panels A and B, illustrate the ability of ultra-short pulses to penetrate tissue heterogeneities. A single plate electrode is placed non-invasively on a region of tissue, and a ground electrode is inserted into the lower left corner of an adjacent region of tissue comprising different electrical properties (in this case, pancreatic tissue and surrounding endothelial layer). Using similar techniques as described in Example 4, the electric field distribution is predicted when 1000 V, 10 µs square-wave pulses and 1000 V, 10 ns square-wave pulses are delivered from the energized electrode. The complex Laplace's equation was solved for 2971 degrees of freedom.

The treatment area (region enclosed by broken line) of the tissue region undergoing IRE around internal ground electrode is shown in the figure. More specifically, 1000 V, 10 µs square-wave pulses (Panel A) and 1000 V, 10 ns square-wave pulses (Panel B) are delivered from the energized electrode placed outside the pancreas along the connective tissue capsule. The thin tissue layer adjacent to the energized electrodes is 10 times less conductive and 10 times more able to store charge than the large tissue region in which the grounded electrode is inserted. The results shown in FIG. 7 indicate that the 10 ns pulses are better suited to bypass the thin tissue layer than the 10 μs pulses. This agrees with the results obtained from the equivalent circuit model presented in the detailed description of various embodiments of the invention section. Further, most of the treatment is concentrated around the ground electrode when 10 ns pulses are employed, sparing a greater amount of the thin tissue layer from treatment. It is also important to note that if the location of the ground electrode is altered, the treatment area is still concentrated around the ground electrode in its altered location.

Figure 16:
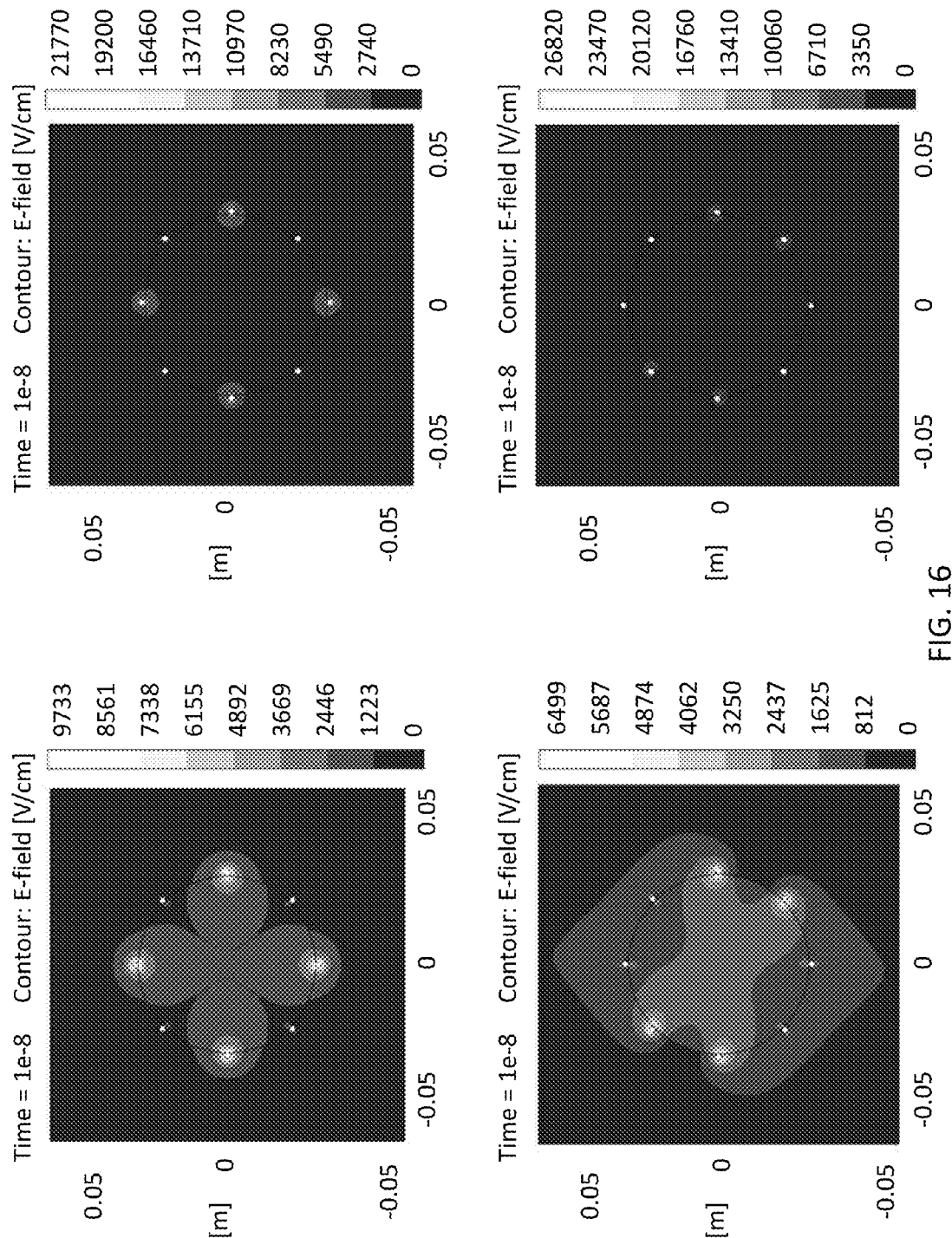
FIG. 16 shows the electric field distribution resulting from the FEM for predicting electric field distribution in a tissue surrounded by an epithelial layer. In the top left, 10 ns pulses are delivered horizontally and vertically across the tissue in an alternating fashion from two pairs of electrodes. This same scenario is shown in the top right for 10 µs pulses. In the bottom left, 10 ns pulses are delivered simultaneously from adjacent electrodes. This same scenario is shown in the bottom right for 10 µs pulses.

The results shown in FIG. 16 extend those presented above for situations in which the epithelial layer is modeled not as a thin layer of tissue, but as a distributed impedance boundary condition representing a continuous lipid bilayer encapsulating the tissue. This model was constructed with techniques similar to those described in Example 4, with the major differences being the two-dimensional nature of the geometry and the presence of spherical electrodes instead of plate electrodes. The first simulation (top left) shows that the characteristic "peanut-shaped" electric field distribution is generated in the tissue when 10 ns pulses are delivered horizontally and vertically across the tissue in an alternating fashion from two pairs of electrodes. The region of tissue in which the "peanuts" overlap is the projected, targeted treatment area, because only cells in that region achieve a TMP above the threshold for electroporation. This same scenario is shown in the top right for 10 μs pulses. In this case, the electric field does not penetrate the epithelial layer, and only cells within the epithelial layer are treated. The second simulation (bottom left) shows the electric field distribution generated when 10 ns pulses are delivered simultaneously from two adjacent electrodes. In this case, the region of tissue between the electrodes of equal current injection is spared from treatment, whereas the center of the tissue is not. This electrode activation pattern is useful for situations in which a sensitive structure such as a major blood vessel or nerve is present between the aforementioned electrodes. This same scenario is shown in the bottom right for 10 μs pulses, and as before, the electric field does not penetrate the epithelial layer, and only cells within the epithelial layer are treated.

Example 7

System for Generating Ultra-short Electric Pulses

Figure 8:
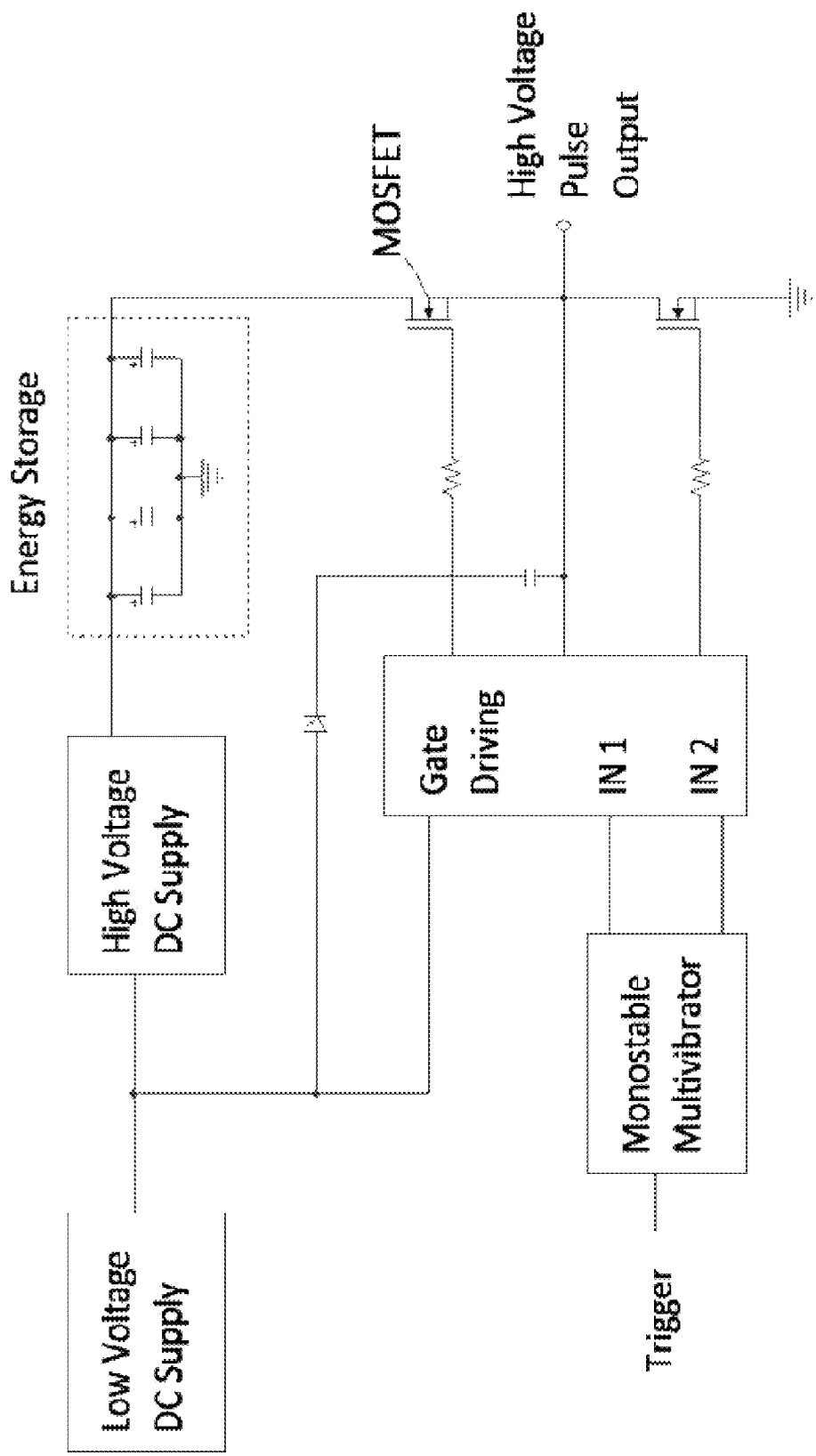
FIG. 8 depicts a schematic of a system to provide ultra-short, high-intensity, electric pulses to a sample according to embodiments of the invention.

FIG. 8 depicts an exemplary high-level diagram of a system to provide ultra-short, high-intensity, electric pulses to a sample. This system relies upon a half-bridge MOSFET configuration that is being driven by a commercial gate-driver integrated circuit. More specifically, FIG. 8 displays an exemplary system having four basic sub-systems, a low voltage power supply, a high voltage power supply with optional energy storage, pulse forming circuitry, and high-voltage switching circuitry. It is to be noted that it is possible to reproduce a similar output with a different number of sub-systems.

Modern semiconductor devices provide an excellent means to produce short electric pulses for high voltage switching. In FIG. 8, two Metal Oxide Semiconductor Field Effect Transistors (MOSFETs) are shown in a half-bridge configuration. This configuration allows the output of the system to be maintained at three possible states, namely: ground (output voltage is zero), high (output voltage is equal to the power supply voltage), and floating (output voltage can assume any value). The half-bridge configuration allows for flexibility in the system but is not absolutely crucial to achieve ultra-short pulses. A single semiconductor operated as a switch could also be used to trigger an ultra-short pulse. Furthermore, MOSFETs are not the only semiconductor devices that can be utilized to produce a pulse. Bipolar Junction Transistors (BJTs), Insulated Gate Bipolar Transistors (IGBTs), and Junction Field Effect Transistors (JFETs) are examples of some of the semiconductor devices that may be used to produce an output pulse FIG. 8 also displays the use of a commercially available gate-driver integrated circuit (IC) coupled with a monostable multivibrator to produce an ultra-short pulse and trigger the proper semiconductor device. This is just one method of translating a trigger signal from the user into a short duration pulse which then turns-on the semiconductor device. Semiconductor device driving can also be accomplished through discrete passive and active components. Similarly, waveform generation for the device does not have to come from a discrete or packaged monostable multivibrator circuit. A pulse may be formed using a computer running suitable software, a microcontroller, digital signal processor, or even a direct digital synthesis IC.

There are a multitude of methods to provide power to the above-mentioned circuitry. FIG. 8 displays separate low and high-voltage power supplies to provide the necessary power for all of the systems elements. Additionally, the high-voltage supply is shown connected to a large bank of output capacitors in order to maintain the output voltage level during the pulse. This large capacitance in just one example of an energy storage method to maintain the output voltage of the power supply during the pulse and may not be required with certain power supply topologies.

Example 8

System for Controlling Multiple Electrodes in Novel Device Designs

Figure 9:
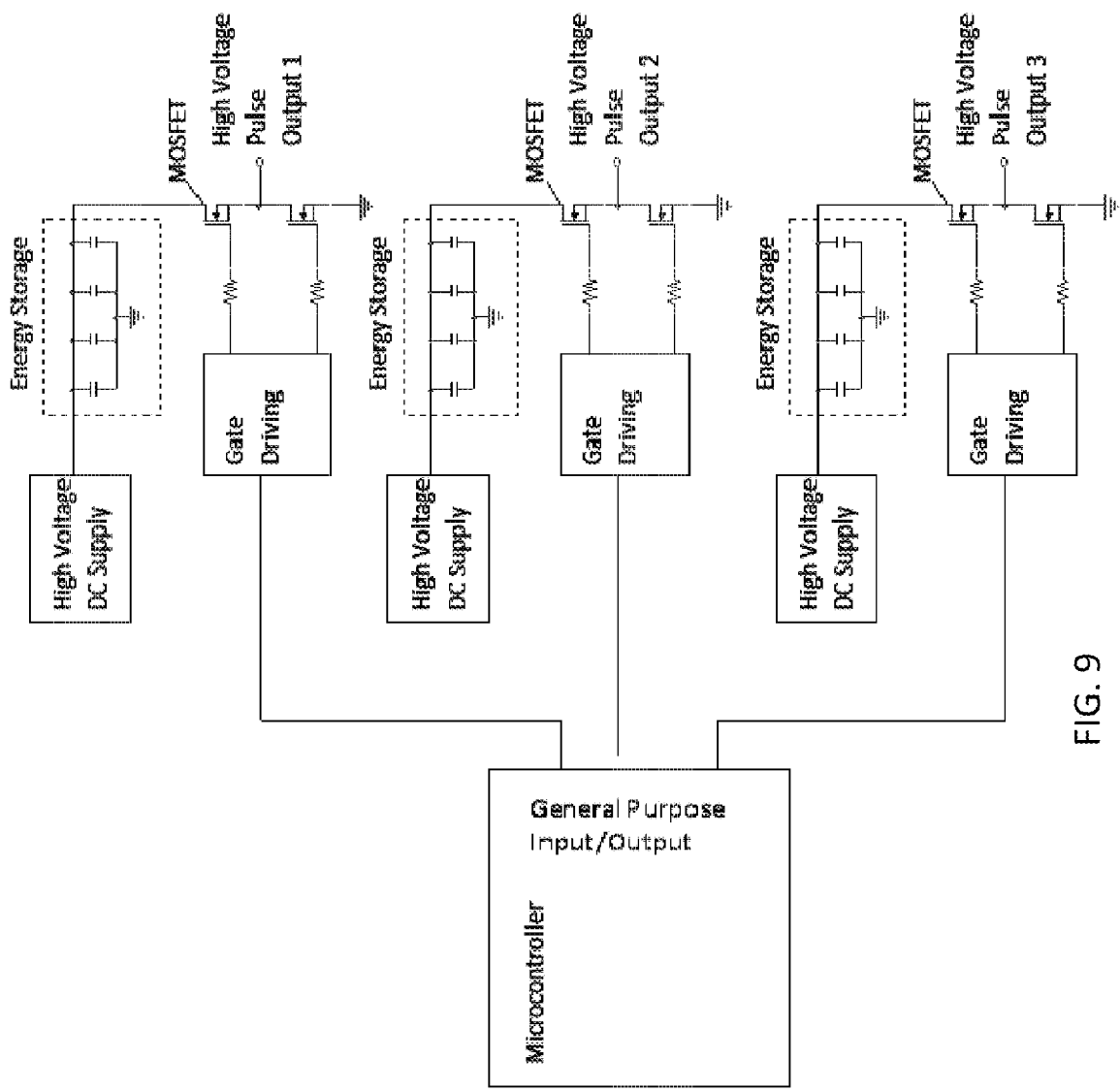
FIG. 9 depicts a schematic of a system having multiple high-voltage pulse outputs.

FIG. 9 illustrates a modular implementation for controlling multiple pulse outputs using a microcontroller. More specifically, FIG. 9 shows a system configuration having multiple high-voltage pulse outputs. Through a modular approach, pulses maybe be applied in different locations with independent durations and intensities. The general purpose input/output pins of a microcontroller can be used to control multiple outputs in order to better tailor a treatment program. By implementing each pulse output as an independent system containing its own power supply, energy storage, and high-voltage switching circuitry, the duration, intensity, and timing of each pulse can be precisely tailored to the desired application.

One method of controlling each pulse output is through the use of the general purpose input/output (GPIO) pins of a microcontroller or digital signal processor. Modern microcontrollers possess a multitude of GPIO pins which a low-voltage pulse can be generated. This low-voltage pulse is then translated into a pulse with the desired intensity by the high-voltage circuitry at each pulse output. In this implementation the pulse length and timing is determined by software running on the microcontroller. Conversely, a similar implementation may be accomplished using a personal computer.

It is also important to note that the method of controlling the timing and pulse duration could be used to directly control the intensity of the output pulse by varying the voltage of each output's power supply. It is through this simultaneous control of multiple outputs that highly flexible treatment programs may be tailored to a patient's individual needs.

Example 9

Figure 17:
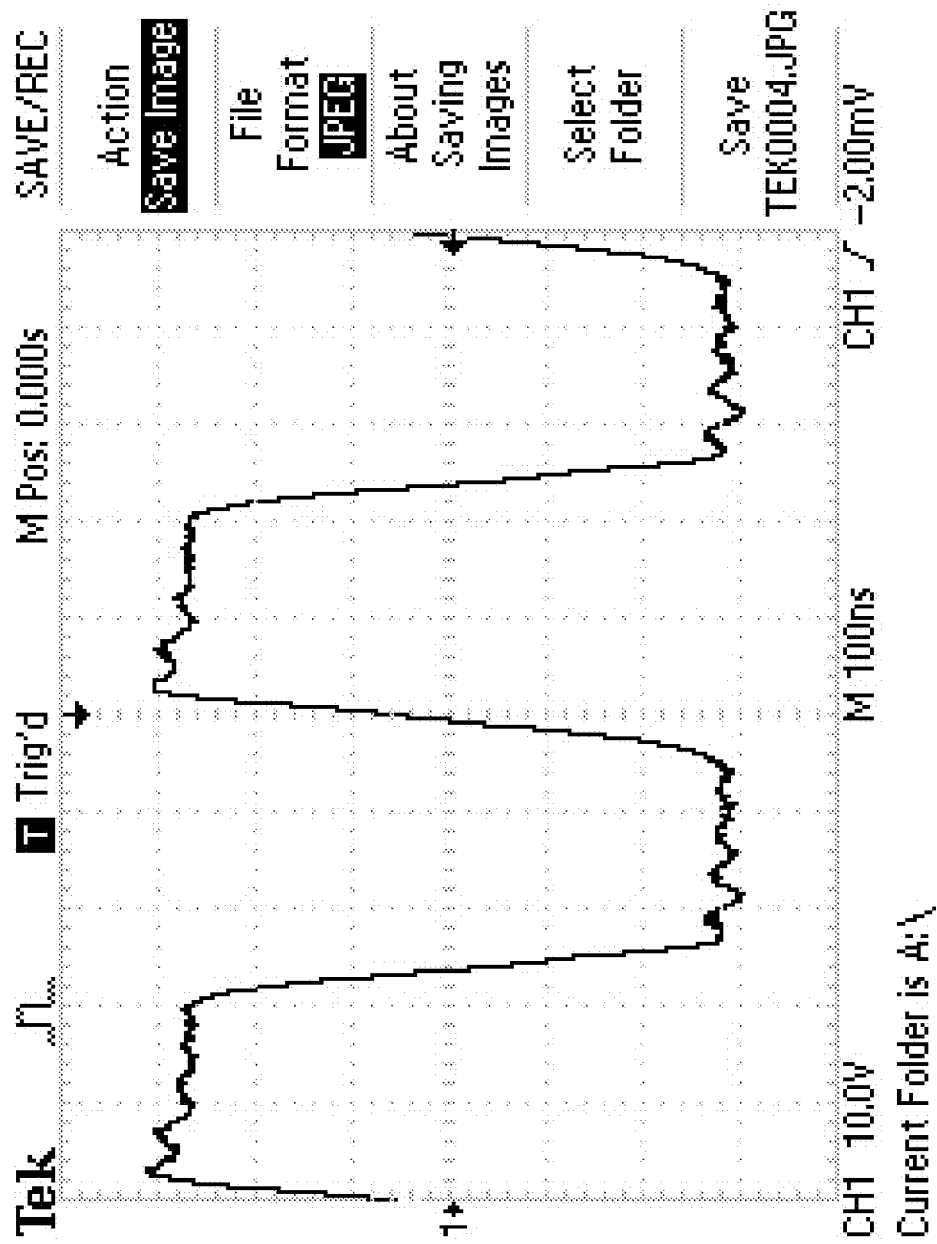
FIG. 17 shows an output waveform by a simple circuit using a wideband amplifier to create ultra-short high frequency pulses.

Demonstration of Varying the Region of Treatment Through the Adjustment of Pulse Parameters The mechanism of the present invention may be demonstrated in vitro by culturing cells on a micro-fabricated electrode array. These cultured cells would then be treated with dyes in order to indicate the state of the cell's viability. By applying pulses to the micro-electrode array the cells grown on the array will undergo electroporation or supra-poration depending on the pulse parameters used in the experiment. The present invention suggests that the location of the treated cells in relation to the electrode array may be changed by adjustment of pulse parameters. The combination of a wideband amplifier with dedicated pulse generation equipment or computer-based pulse generation equipment would allow for the investigation of the effect of various pulse parameters on the region of effected cells. The use of a wideband amplifier to create ultra-short high frequency pulses has been demonstrated as a viable method and the output waveform produced by a simple circuit is shown in FIG. 17. By performing this experiment at the microscope scale, much lower voltages may be used and the use of a wideband amplifier would also allow for much higher pulse repetition frequencies than dedicated switched-semiconductor devices.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

The invention claimed is:

1. A method of treating a subject suffering from an aberrant cell growth, said method comprising:
   implanting an electrode into or adjacent the aberrant growth region within the body of a subject, and
   causing a train of electrical pulses to be emitted from the electrode into the aberrant growth region, wherein each individual pulse in the pulse train is incapable of IRE alone but together as the pulse train capable of causing predominately non-thermal killing of aberrantly growing cells by IRE.

2. The method of claim 1, wherein the pulse train is between 50 nanoseconds and 10,000 nanoseconds.

3. The method of claim 1, wherein two or more electrodes are used in the method and are provided as part of a single device.

4. The method of claim 1, wherein two or more electrodes are used in the method.

5. The method of claim 4, further comprising positioning the electrodes at a distance apart from each other to create custom treatment area shapes through varying electrode activation patterns.

6. The method of claim 1, wherein the aberrant cell growth is a neoplasia.

7. The method of claim 6, wherein the neoplasia is leukemia or pancreatic cancer.

8. The method of claim 1, wherein the subject is a human.

9. The method of claim 1, wherein the implanted electrode is a current input electrode and wherein a current return electrode is implanted within the body of the subject at a site adjacent to or distant from the aberrant growth region, or is provided external to the subject.

10. The method of claim 1, wherein the implanted electrode is a return electrode and wherein a current input electrode is implanted within the body of the subject at a site adjacent to or distant from the aberrant growth region, or is provided external to the subject.

11. The method of claim 1, wherein the step of causing a train of pulses includes causing a train of pulses to be emitted with each pulse having a pulse width of 10 microseconds or less and a delay between two adjacent pulses.

12. The method of claim 1, wherein the method results in a reduction in the size of a tumor.

13. The method of claim 12, wherein the method results in ablation of the tumor.

14. The method of claim 1, comprising:
   implanting multiple electrodes into or adjacent the aberrant growth region within the body of a subject;
   causing multiple electrical pulses to be emitted from varying electrodes at multiple positions of targeted tissue, wherein an individual pulse from one electrode is insufficient to cause IRE, but wherein temporal and spatial summation of such pulses yields ablation zones where the effective fields overlap.

15. The method of claim 1, wherein causing multiple electrical pulses to be emitted from the electrode comprises emitting multiple electric pulses such that the temporal and spatial summation of such pulses results in the generation of an electric field of about 1 kV/cm to 50 kV/cm for 1000 nanoseconds or less to induce supra-poration in addition to IRE.

16. The method of claim 1, wherein the individual electric pulses are monophasic.

17. The method of claim 1, wherein the individual electric pulses are biphasic.

18. The method of claim 1, wherein a train of monophasic pulses is delivered in one direction, followed by a subsequent pulse train of opposite polarity.

19. The method of claim 1, wherein the waveforms for the electric pulses are triangular, square, sinusoidal, exponential, or trapezoidal.

20. The method of claim 1, wherein the electrode is connected to a system for employing electrical impedance tomography (EIT), computer tomography (CT), Magnetic Resonance Imaging (MRI), or ultrasound to image the tissue prior to treatment by applying small alternating currents that themselves do not damage the tissue.

21. A method of treating a subject suffering from an aberrant cell growth, said method comprising:
   contacting the subject with a first electrode,
   placing at least two additional electrodes outside the subject's body at positions that permit electrical charges to be delivered to the aberrant cell growth, and
   causing a train of electrical pulses to be emitted from one or more of the electrodes into the aberrant growth region in, wherein each pulse is incapable of IRE alone but together as the pulse train capable of causing predominately non-thermal killing of aberrantly growing cells by IRE.

22. The method of claim 21, wherein contacting comprises contacting the first electrode with the skin of the subject.

23. The method of claim 21, wherein contacting comprises implanting the first electrode at a site in the subject's body that is adjacent to the aberrant cell growth.

24. The method of claim 21, which is a method of delivering an electric pulse through a layer, wherein the pulse train is between 50 nanoseconds and 10,000 nanoseconds.

25. The method of claim 21, wherein the layer is bone, muscle, fat, connective tissue, nervous tissue, or an endothelial layer.

26. The method of claim 21, wherein the pulses induce a combination of both IRE and supra-poration.

27. A method of treating a subject suffering from an aberrant growth, said method comprising:
- implanting an electrode into or adjacent the aberrant growth, and
- causing a train of electrical pulses to be emitted from the electrode into the aberrant growth in, wherein each pulse is incapable of reversible electroporation alone,
- wherein the pulse train is capable of causing reversible electroporation of cells of the aberrant growth and/or cells adjacent the aberrant growth, which results in uptake of bioactive substances into the treated cells.

* * * * *